(12) United States Patent
Kim et al.

(10) Patent No.: US 10,823,589 B2
(45) Date of Patent: Nov. 3, 2020

(54) ELECTRONIC DEVICE AND METHOD FOR CONTROLLING SENSITIVITY OF SENSOR ON BASIS OF WINDOW ATTRIBUTES

(71) Applicant: Samsung Electronics Co., Ltd., Gyeonggi-do (KR)

(72) Inventors: Jong-Ah Kim, Gyeonggi-do (KR); Dong-Han Lee, Gyeonggi-do (KR); Jeong-Ho Cho, Gyeonggi-do (KR); Hee-Woong Yoon, Seoul (KR); Tae-Ho Kim, Chungcheongbuk-do (KR); Jeong-Min Park, Gyeonggi-do (KR)

(73) Assignee: Samsung Electronics Co., Ltd., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 21 days.

(21) Appl. No.: 15/982,161

(22) Filed: May 17, 2018

(65) Prior Publication Data
US 2018/0348024 A1    Dec. 6, 2018

(30) Foreign Application Priority Data

Jun. 2, 2017    (KR) .......................... 10-2017-0069143

(51) Int. Cl.
*G09G 3/19*    (2006.01)
*G01D 18/00*    (2006.01)
(Continued)

(52) U.S. Cl.
CPC ............. *G01D 18/006* (2013.01); *A61B 3/14* (2013.01); *G01D 3/022* (2013.01); *G01D 3/024* (2013.01);
(Continued)

(58) Field of Classification Search
CPC ............. G09G 3/38; G09G 3/19; G06F 3/038
See application file for complete search history.

(56) References Cited

U.S. PATENT DOCUMENTS 9,903,975 B1 * 2/2018 Smoot ...................... G01V 3/02
2009/0225022 A1 * 9/2009 Tolbert .................. G02F 1/1506
345/105
(Continued)

FOREIGN PATENT DOCUMENTS

KR    10-2011-0015959 A    2/2011

*Primary Examiner* — Dennis P Joseph
(74) *Attorney, Agent, or Firm* — Cha & Reiter, LLC.

(57) ABSTRACT

Various embodiments related to an electronic device and a method for controlling sensitivity of a sensor on the basis of window attributes are described. According to an embodiment, an electronic device may include: a housing; a window cover housed in the housing, in which an attribute of at least a partial area may be changed via an electrical control on the basis of at least one attribute; at least one sensor disposed below at least the partial area; and at least one processor, wherein the at least one processor is configured to identify control information related to an operation of changing the attribute of at least the partial area on the basis of the at least one attribute, to determine a sensitivity related to the at least one sensor corresponding to the at least one attribute at least on the basis of the control information, and to acquire peripheral information of the exterior of the electronic device by using the at least one sensor, at least on the basis of the determined sensitivity.

11 Claims, 14 Drawing Sheets

(51) Int. Cl.
*G01D 3/02* (2006.01)
*G01D 3/024* (2006.01)
*G01J 1/44* (2006.01)
*A61B 3/14* (2006.01)
*G01N 21/59* (2006.01)
*H03K 17/945* (2006.01)
*G01N 21/55* (2014.01)
*G01J 1/04* (2006.01)
*G01J 1/02* (2006.01)
*G01D 3/036* (2006.01)
*G01J 1/26* (2006.01)
*G01D 21/00* (2006.01)
*H04M 1/02* (2006.01)
*G01J 1/42* (2006.01)

(52) U.S. Cl.
CPC ........... *G01D 3/0365* (2013.01); *G01D 21/00* (2013.01); *G01J 1/0204* (2013.01); *G01J 1/0219* (2013.01); *G01J 1/0228* (2013.01); *G01J 1/0407* (2013.01); *G01J 1/0488* (2013.01); *G01J 1/26* (2013.01); *G01J 1/4204* (2013.01); *G01J 1/44* (2013.01); *G01N 21/55* (2013.01); *G01N 21/59* (2013.01); *H03K 17/945* (2013.01); *H04M 1/026* (2013.01); *G01J 2001/444* (2013.01); *H04M 1/0266* (2013.01); *H04M 2250/12* (2013.01)

(56) References Cited

U.S. PATENT DOCUMENTS

| | | |
|---|---|---|
| 2010/0164479 A1 | 7/2010 | Alameh et al. |
| 2014/0062896 A1 | 3/2014 | Vieta |
| 2015/0269419 A1* | 9/2015 | Bae .................... G06K 9/00604 382/117 |
| 2017/0031224 A1 | 2/2017 | Gil et al. |

\* cited by examiner

Transmission measurement of EV at different potentials

ELECTRONIC DEVICE AND METHOD FOR CONTROLLING SENSITIVITY OF SENSOR ON BASIS OF WINDOW ATTRIBUTES

CROSS-REFERENCE TO RELATED APPLICATION

This application is based on and claims priority under 35 U.S.C. § 119 of Korean Patent Application No. 10-2017-0069143, filed on Jun. 2, 2017, in the Korean Intellectual Property Office, the disclosure of which is incorporated herein by reference in its entirety.

BACKGROUND

1. Filed

Various embodiments relate to a sensor of an electronic device.

2. Description of the Related Art

Due to the recent remarkable development of information communication technology and semiconductor technology, the spread and use of various electronic devices are rapidly increasing. Particularly, recent electronic devices are portable and capable of communication. The presence of chromatic material in the display can cause sensors to malfunctions.

SUMMARY

The optical-based sensors can perform the sensing operations on the basis of a sensitivity according to predetermined conditions, and when the surrounding environment is different from the predetermined conditions, the sensitivity may deteriorate and sensing performances may be degraded.

For example, when an optically-based sensor is disposed around a structure that may affect light sensing among various positions in an electronic device, a sensitivity may deteriorate and a sensing performance may be degraded due to the structure affecting light sensing. For example, the structure that may affect light sensing may be a window cover having attributes, such as a color, a texture, or a pattern, which may be changed by an electrical signal, or may be a display in which a displayed color or brightness may be changed.

Various embodiments of the present disclosure may provide an electronic device and a method for controlling sensitivity of a sensor on the basis of window attributes, which may prevent degrading of a sensing performance of an optical-based sensor by adjusting a sensitivity of the optical-based sensor on the basis of changes in attributes of a window cover.

Various embodiments may provide an electronic device and a method for controlling sensitivity of a sensor on the basis of window attributes, which may prevent degrading of a sensing performance of an optical-based sensor by adjusting a sensitivity of the optical-based sensor on the basis of changes in displaying attributes of a display screen.

According to various embodiments, an electronic device can comprise a housing; a window cover housed in the housing, wherein an attribute of at least a partial area of a window cover may be changed via an electrical control; at least one sensor disposed below at least the partial area; and at least one processor, wherein the at least one processor is configured to: identify control information related to changing the attribute of at least the partial area of the window cover; determine a sensitivity related to the at least one sensor corresponding to the at least one attribute at least on the basis of the control information; and acquire peripheral information about the outside of the electronic device by using the at least one sensor, at least on the basis of the determined sensitivity.

According to various embodiments, an electronic device comprises: a display; at least one sensor disposed below at least a partial area of the display; and at least one processor, wherein the at least one processor is configured to: identify control information related to displaying of at least the partial area; determine a sensitivity related to the at least one sensor at least on the basis of the control information; and acquire peripheral information of the outside of the electronic device by using the at least one sensor, at least on the basis of the determined sensitivity.

According to various embodiments, in an electronic device, a sensitivity of the optical-based sensor is adjusted to reflect an effect of light on the optical-based sensor, the light according to a color, a texture, and a pattern of a window cover, on the basis of changes in attributes of the window cover.

Further, according to various embodiments, degradation of sensing performance of an optical-based sensor can be prevented by adjusting a sensitivity of the optical-based sensor on the basis of change in an attribute of a display so that an effect of light on the optical-based sensor, which corresponds to a color and brightness of the display, is reflected.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
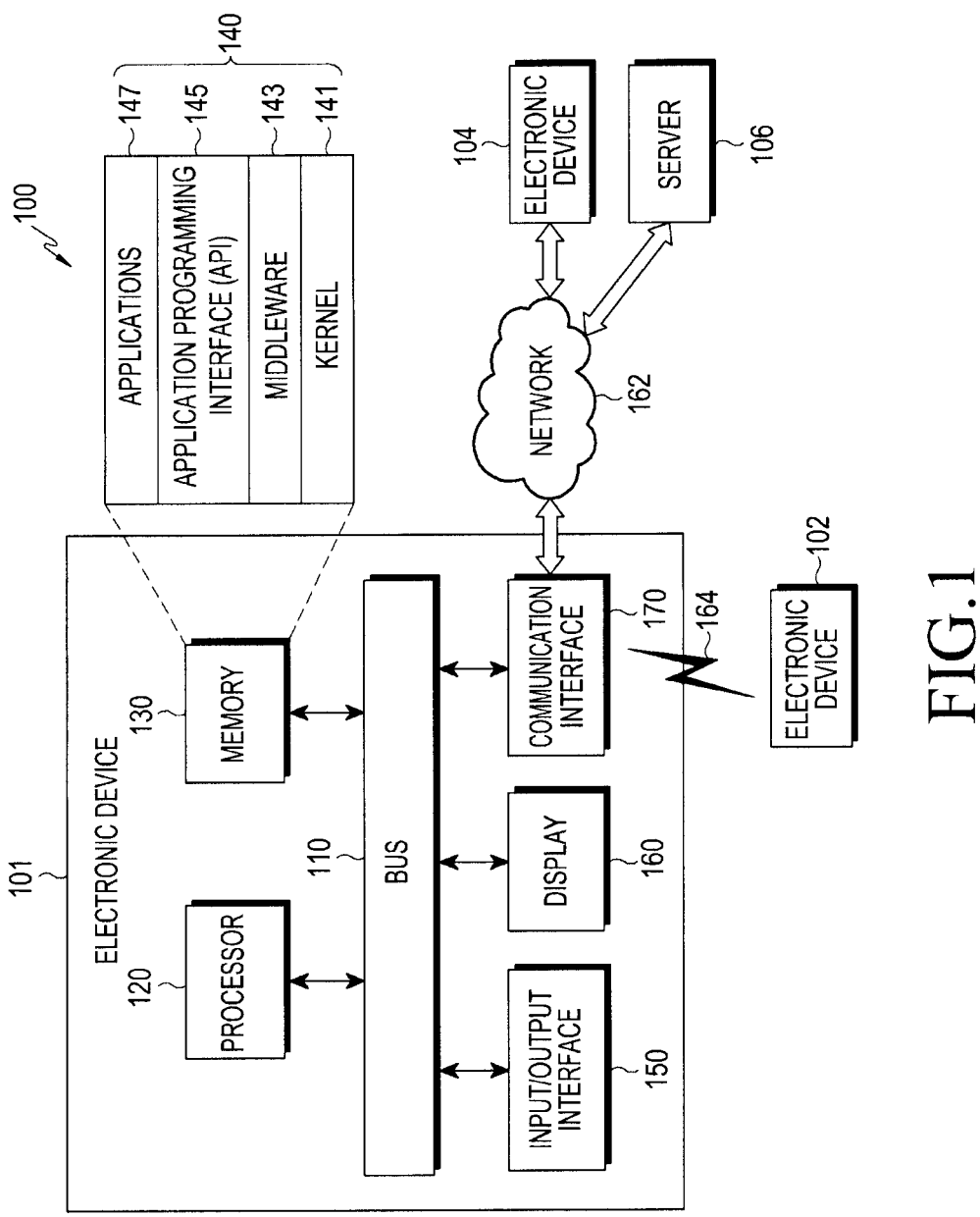
FIG. 1 is a block diagram illustrating a network environment including an electronic device according to various embodiments.

Hereinafter, various embodiments will be described with reference to the accompanying drawings. The embodiments and the terms used therein are not intended to limit the technology disclosed herein to specific forms, and should be understood to include various modifications, equivalents, and/or alternatives to the corresponding embodiments. In describing the drawings, similar reference numerals may be used to designate similar constituent elements. A singular expression may include a plural expression unless they are definitely different in a context. In this document, expressions such as A or B or at least one of A and/or B include all possible combinations of items listed together. The expression "a first", "a second", "the first", or "the second" used in various embodiments may modify various components regardless of the order and/or the importance but does not limit the corresponding components. When an element (e.g., first element) is referred to as being "(functionally or communicatively) connected to", or "directly coupled" another element (second element), the element may be connected directly to the another element or connected to the another element through yet another element (e.g., third element).

The expression "configured to" as used in various embodiments may be interchangeably used with, for example, "suitable for", "having the capacity to", "designed to", "adapted to", "made to", or "capable of" in terms of hardware or software, according to circumstances. Alternatively, in some situations, the expression "device configured to" may mean that the device, together with other devices or components, "is able to". For example, the phrase "processor adapted (or configured) to perform A, B, and C" may mean a dedicated processor (e.g., embedded processor) only for performing the corresponding operations or a generic-purpose processor (e.g., Central Processing unit (CPU) or Application Processor (AP)) that can perform the corresponding operations by executing one or more software programs stored in a memory device.

An electronic device according to various embodiments may include at least one of, for example, a smart phone, a tablet Personal Computer (PC), a mobile phone, a video phone, an electronic book reader, a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit). In some embodiments, the electronic device may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

In other embodiments, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Navigation Satellite System (GNSS), an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, a drone, an Automatic Teller's Machine (ATM) in banks, Point Of Sales (POS) in a shop, or internet device of things (e.g., a light bulb, various sensors, a sprinkler device, a fire alarm, a thermostat, a streetlamp, a toaster, a sporting goods, a hot water tank, a heater, a boiler, etc.). According to some embodiments, an electronic device may include at least one of a part of furniture, a building/structure, or a vehicle, an electronic board, an electronic signature receiving device, a projector, and various types of measuring instruments (e.g., a water meter, an electric meter, a gas meter, a radio wave meter, and the like). In various embodiments, the electronic device may be flexible, or may be a combination of one or more of the aforementioned various devices. The electronic device according to one embodiment is not limited to the above described devices. In the present disclosure, the term "user" may indicate a person using an electronic device or a device (e.g., an artificial intelligence electronic device) using an electronic device.

An electronic device 101 within a network environment 100 according to various embodiments will be described with reference to FIG. 1. The electronic device 101 may include a bus 110, a processor 120, a memory 130, an input/output interface 150, a display 160, and a communication interface 170. In some embodiments, the electronic device 101 may omit at least one of the elements, or may further include other elements. The bus 110 may connect elements 110-170 each other, and may include a circuit that transfers communication between the elements (e.g., a control message or data). The processor 120 may include one or more among a central processing unit, an application processor, a communication processor (CP). The processor 120, for example, may carry out operations or data processing relating to the control and/or communication of at least one other element of the electronic device 101.

The memory 130 may include a volatile and/or non-volatile memory. The memory 130 may store, for example, instructions or data relevant to at least one other element of the electronic device 101. According to an embodiment, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an operating system. The kernel 141 may control or manage system resources (e.g., the bus 110, the processor 120, or the memory 130) used for executing an operation or function implemented by other programs (e.g., the middleware 143, the API 145, or the application 147). Furthermore, the kernel 141 may provide an interface through which the middleware 143, the API 145, or the application programs 147 may access the individual elements of the electronic device 101 to control or manage the system resources.

The middleware 143 may function as, for example, an intermediary for allowing the API 145 or the application programs 147 to communicate with the kernel 141 to exchange data. Furthermore, the middleware 143 may process one or more task requests, which are received from the application programs 147, according to priorities thereof. For example, the middleware 143 may assign priorities for using the system resources (e.g., the bus 110, the processor 120, the memory 130, or the like) of the electronic device 101 to one or more of the application programs 147, and may process the one or more task requests. The API 145 is an interface through which the applications 147 control functions provided from the kernel 141 or the middleware 143, and may include, for example, at least one interface or function (e.g., instruction) for file control, window control, image processing, or text control. For example, the input/ output interface 150 may forward instructions or data, input from a user or an external device, to the other element(s) of the electronic device 101, or may output instructions or data, received from the other element(s) of the electronic device 101, to the user or the external device.

The display 160 may include, for example, a Liquid Crystal Display (LCD), a Light Emitting Diode (LED) display, an Organic Light Emitting Diode (OLED) display, a Micro Electro Mechanical System (MEMS) display, or an electronic paper display. The display 160 may display, for example, various types of content (e.g., text, images, videos, icons, and/or symbols) for a user. The display 160 may include a touch screen and may receive, for example, a touch, gesture, proximity, or hovering input using an electronic pen or the user's body part. The communication interface 170, for example, may set communication between the electronic device 101 and an external device (e.g., a first external electronic device 102, a second external electronic device 104, or a server 106). For example, the communication interface 170 may be connected to a network 162 through wireless or wired communication to communicate with the external device (e.g., the second external electronic device 104 or the server 106).

The wireless communication may include, for example, a cellular communication that uses at least one of LTE, LTE-Advance (LTE-A), Code Division Multiple Access (CDMA), Wideband CDMA (WCDMA), Universal Mobile Telecommunications System (UMTS), Wireless Broadband (WiBro), Global System For Mobile Communications (GSM), or the like. According to an embodiment, as exemplified as short-range communication 164 of FIG. 1, the wireless communication may include at least one of Wireless Fidelity (WiFi), Lite Fidelity (LiFi), Bluetooth, Bluetooth Low power (BLE), ZigBee, Near Field Communication (NFC), Magnetic Secure Transmission, Radio Frequency (RF), or Body Area Network (BAN). According to an embodiment, the wired communication may include GNSS. The GNSS may be, for example, a Global Positioning System (GPS), a Global Navigation Satellite System (Glonass), a Beidou Navigation Satellite System (hereinafter, referred to as "Beidou"), or Galileo (the European global satellite-based navigation system). Hereinafter, in this document, the term "GPS" may be interchangeable with the term "GNSS". The wired communication may include, for example, at least one of a Universal Serial Bus (USB), a High Definition Multimedia Interface (HDMI), Recommended Standard 232 (RS-232), a power line communication, a Plain Old Telephone Service (POTS), etc. The network 162 may include at least one of a telecommunications network, for example, a computer network (e.g., LAN or WAN), the Internet, and a telephone network.

Each of the first and second external electronic devices 102 and 104 may be of a type identical to or different from that of the electronic device 101. According to various embodiments, all or some of the operations executed in the electronic device 101 may be executed in another electronic device or a plurality of electronic devices (e.g., the electronic devices 102 and 104 or the server 106). According to an embodiment, when the electronic device 101 has to perform some functions or services automatically or in response to a request, the electronic device 101 may make a request for performing at least some functions relating thereto to another device (e.g., the electronic device 102 or 104 or the server 106) instead of performing the functions or services by itself or in addition. Another electronic device (e.g., the electronic device 102 or 104, or the server 106) may execute the requested functions or the additional functions, and may transfer information about the result of the execution to the electronic device 101. The electronic device 101 may provide the received result as it is or additionally process the received result and provide the requested functions or services. To achieve this, for example, cloud computing, distributed computing, or client-server computing technology may be used.

The display will be described in further detail in FIGS. 5-7, and can include or form a portion of a changeable window cover. The changeable window cover can include an attribute changing element, such as electrochromic material. As a result of this changes in the attributes of the attribute changing material, the one or more processors 120 can identify control information associated with the changed attribute to determine the sensitivity related to the one sensor.

Figure 2:
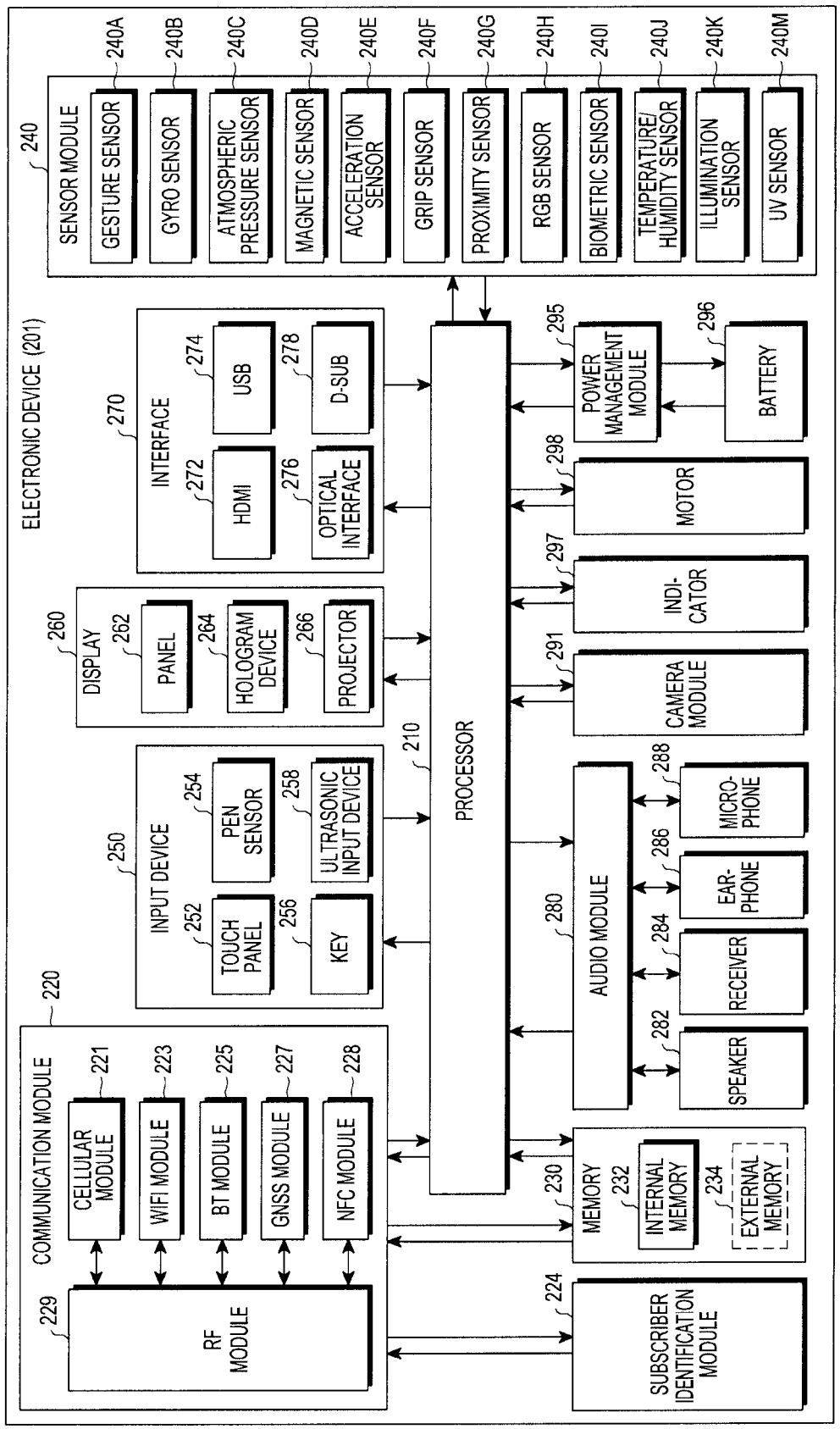
FIG. 2 is a block diagram of an electronic device according to various embodiments.

FIG. 2 is a block diagram of an electronic device according to various embodiments.

The electronic device 201 may include, for example, the whole or part of the electronic device 101 illustrated in FIG. 1. The electronic device 201 may include at least one processor 210 (e.g., an AP), a communication module 220, a subscriber identification module 224, a memory 230, a sensor module 240, an input device 250, a display 260, an interface 270, an audio module 280, a camera module 291, a power management module 295, a battery 296, an indicator 297, and a motor 298. The processor 210 may control a plurality of hardware or software elements connected thereto and may perform various data processing and operations by driving an operating system or an application program. The processor 210 may be implemented by, for example, a System on Chip (SoC). According to an embodiment, the processor 210 may further include a Graphic Processing Unit (GPU) and/or an image signal processor. The processor 210 may also include at least some of the elements illustrated in FIG. 2 (e.g., a cellular module 221). The processor 210 may load, in a volatile memory, instructions or data received from at least one of the other elements (e.g., a non-volatile memory), process the loaded instructions or data, and store the result data in the non-volatile memory.

The communication module 220 may have a configuration that is the same as or similar to that of the communication interface 170. The communication module 220 may include, for example, a cellular module 221, a Wi-Fi module 223, a Bluetooth module 225, a GNSS module 227, an NFC module 228, and an RF module 229. The cellular module 221 may provide, for example, a voice call, a video call, a text message service, an Internet service, or the like through a communication network. According to an embodiment, the cellular module 221 may identify and authenticate the electronic device 201 within a communication network using the subscriber identification module 224 (e.g., a SIM card). According to an embodiment, the cellular module 221 may perform at least some of the functions that the processor 210 may provide. According to an embodiment, the cellular module 221 may include a communication processor (CP). According to some embodiments, at least some (e.g., two or more) of the cellular module 221, the Wi-Fi module 223, the BT module 225, the GNSS module 227, and the NFC module 228 may be included in one Integrated Chip (IC) or IC package. The RF module 22F may transmit/receive, for example, a communication signal (e.g., an RF signal). The RF module 229 may include, for example, a transceiver, a Power Amp Module (PAM), a frequency filter, a Low Noise Amplifier (LNA), an antenna, or the like. According to another embodiment, at least one of the cellular module 221, the Wi-Fi module 223, the BT module 225, the GPS module 227, and the NFC module 228 may transmit/receive an RF signal through a separate RF module. The subscriber identification module 224 may include, for example, a card that includes a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an internal memory 232 or an external memory 234. The internal memory 232 may include, for example, at least one of a volatile memory (e.g., a DRAM, an SRAM, an SDRAM, or the like) and a non-volatile memory (e.g., a One Time Programmable ROM (OTPROM), a PROM, an EPROM, an EEPROM, a mask ROM, a flash ROM, a flash memory, a hard disc drive, or a Solid State Drive (SSD)). The external memory 234 may include a flash drive, for example, a Compact Flash (CF), a Secure Digital (SD), a Micro-SD, a Mini-SD, an eXtreme Digital (xD), a MultiMedia Card (MMC), a memory stick, and the like. The external memory 234 may be functionally or physically connected to the electronic device 201 through various interfaces.

The sensor module 240 may, for example, measure a physical quantity or detect the operating state of the electronic device 201 and may convert the measured or detected information into an electrical signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G a color sensor 240H (e.g., a Red, Green, and Blue (RGB) sensor), a biometric sensor 240I, a temperature/humidity sensor 240J, an illuminance sensor 240K, and a ultraviolet (UV) sensor 240M. Additionally or alternatively, the sensor module 240 may include, for example, an e-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling one or more sensors included therein. In some embodiments, the electronic device 201 may further include a processor, which is configured to control the sensor module 240, as a part of the processor 210 or separately from the processor 210 in order to control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer to provide a tactile reaction to a user. The (digital) pen sensor 254 may be, for example, a part of the touch panel or may include a separate recognition sheet. The key 256 may include, for example, a physical button, an optical key, or a keypad. The ultrasonic input device 258 may detect ultrasonic waves, which are generated by an input tool, through a microphone (e.g., a microphone 288) and may identify data corresponding to the detected ultrasonic waves.

The display 260 (e.g., the display 160) may include a panel 262, a hologram device 264, a projector 266, and/or a control circuit for controlling the same. The panel 262 may be implemented to be, for example, flexible, transparent, or wearable. The panel 262 may include the touch panel 252, and one or more modules. According to an embodiment, the panel 262 may include a pressure sensor (or a POS sensor) which may measure a strength of pressure of a user's touch. The pressure sensor may be integrated with the touch panel 252 or may be implemented as one or more sensors separate from the touch panel 252. The hologram device 264 may show a three-dimensional image in the air by using an interference of light. The projector 266 may display an image by projecting light onto a screen. The screen may be located, for example, in the interior of, or on the exterior of, the electronic device 201. The interface 270 may include, for example, an HDMI 272, a USB 274, an optical interface 276, or a D-subminiature (D-sub) 278. The interface 270 may be included in, for example, the communication circuit 170 illustrated in FIG. 1. Additionally or alternatively, the interface 270 may include, for example, a Mobile High-Definition Link (MHL) interface, a Secure Digital (SD) card/Multi-Media Card (MMC) interface, or an Infrared Data Association (IrDA) standard interface.

The audio module 280 may convert, for example, sound into an electrical signal, and vice versa. At least some elements of the audio module 280 may be included, for example, in the input/output interface 150 illustrated in FIG. 1. The audio module 280 may process sound information that is input or output through, for example, a speaker 282, a receiver 284, earphones 286, the microphone 288, and the like. The camera module 291 is a device that can photograph a still image and a moving image. According to an embodiment, the camera module 291 may include one or more image sensors (e.g., a front sensor or a rear sensor), a lens, an image signal processor (ISP), or a flash (e.g., an LED or xenon lamp). The power management module 295 may manage, for example, the power of the electronic device 201. According to an embodiment, the power management module 295 may include a Power Management Integrated Circuit (PMIC), a charger IC, or a battery or fuel gauge. The PMIC or the charger IC may have a wired and/or wireless charging method. Examples of the wireless charging method may include a magnetic resonance method, a magnetic induction method, an electromagnetic wave method, and the like. Additional circuits (e.g., a coil loop, a resonance circuit, a rectifier, and the like) for wireless charging may be further included. The battery gauge may measure, for example, a residual quantity of the battery 296, and a voltage, a current, or a temperature while charging. The battery 296 may include, for example, a rechargeable battery or a solar battery.

The indicator 297 may display a particular state, for example, a booting state, a message state, a charging state, or the like of the electronic device 201 or a part (e.g., the processor 210) of the electronic device 201. The motor 298 may convert an electrical signal into mechanical vibration, and may generate vibration, a haptic effect, or the like. The electronic device 201 may include a mobile TV support device that can process media data according to a standard, such as Digital Multimedia Broadcasting (DMB), Digital Video Broadcasting (DVB), mediaFlo™, and the like. Each of the above-described component elements of hardware according to the present disclosure may be configured with one or more components, and the names of the corresponding component elements may vary on the basis of the type of electronic device. In various embodiments, an electronic device (e.g., the electronic device 201) may omit some elements or may further include additional elements, or some of the elements of the electronic device may be combined with each other to configure one entity, in which case the electronic device may identically perform the functions of the corresponding elements prior to the combination.

The display 260 may be disposed under a window cover and one or more of the sensors 240 may be disposed below the window cover. The window cover may include a portion which may operate as a touch panel 252, and can further include an attribute changing element, such as electrochromic material. As a result of this changes in the attributes of the attribute changing material, the at least one processors 210 can identify control information associated with the changed attribute to determine the sensitivity related to the one or more sensors 240.

For example, the attribute changing material can change hues, texture or patterns, changing the light receiving properties of window cover. As a result, the light that is incident on an RGB sensor 240H is altered. The at least one processor 210 identifies control information related to the changed hues, texture, or patterns, and determines a sensitivity related to the RGB sensor. The electronic device 100 acquires RGB information about the outside of the electronic device 100 on the basis of the changed sensitivity of the RGB sensor.

In another embodiment, the attribute changing material can change hues, texture or patterns, changing the light receiving properties of window cover. As a result, the light that is incident on an illumination sensor 240K is altered. The at least one processor 210 identifies control information related to the changed hues, texture, or patterns, and determines a sensitivity related to the illumination sensor 240K. The electronic device 100 acquires light information about the outside of the electronic device 100 on the basis of the changed sensitivity of the illumination sensor 240K.

In another embodiment, the attribute changing material can change hues, texture or patterns, changing the light receiving properties of window cover. As a result, reflected light from an external object that is incident on a proximity sensor 240G is altered. The at least one processor 210 identifies control information related to the changed hues, texture, or patterns, and determines a sensitivity related to the proximity sensor 240G. The electronic device 100 acquires light information about the outside of the electronic device 100 on the basis of the changed sensitivity of the proximity sensor 240G.

Figure 3:
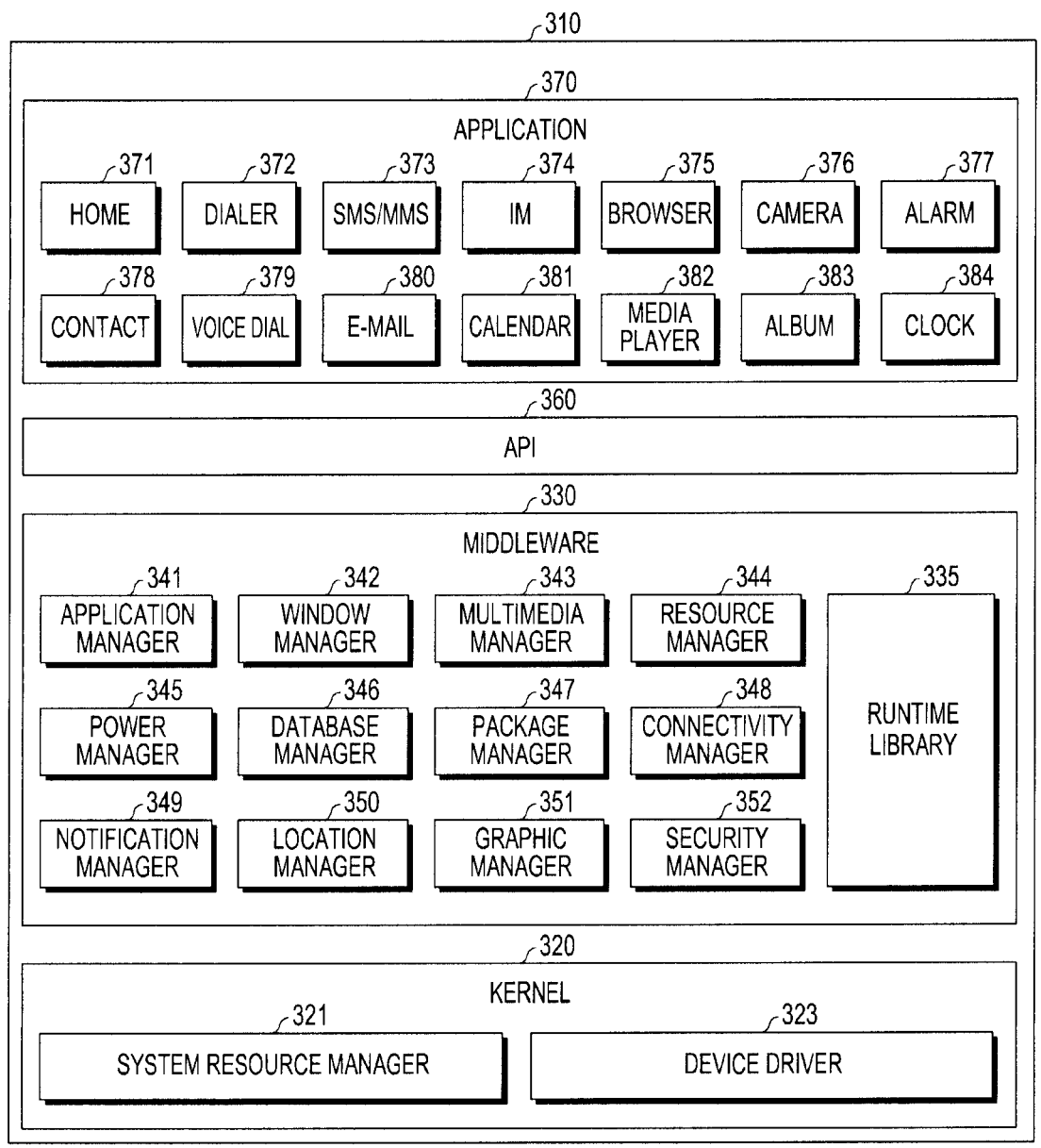
FIG. 3 is a block diagram of a program module according to various embodiments.

FIG. 3 is a block diagram of a program module according to various embodiments.

According to an embodiment, the program module 310 (e.g., the program 140) may include an Operating System (OS) that controls resources relating to an electronic device (e.g., the electronic device 101) and/or various applications (e.g., the application programs 147) that are driven on the operating system. The operating system may include, for example, Android™, iOS™, Windows™, Symbian™, Tizen™, or Bada™. Referring to FIG. 3, the program module 310 may include a kernel 320 (e.g., the kernel 141), middleware 330 (e.g., the middleware 143), an API 360 (e.g., the API 145), and/or applications 370 (e.g., the application programs 147). At least a part of the program module 310 may be preloaded on the electronic device, or may be downloaded from an external electronic device (e.g., the electronic device 102 or 104 or the server 106).

The kernel 320 may include, for example, a system resource manager 321 and/or a device driver 323. The system resource manager 321 may control, allocate, or retrieve system resources. According to an embodiment, the system resource manager 321 may include a process manager, a memory manager, or a file system manager. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver. The middleware 330 may provide, for example, a function required by the applications 370 in common, or may provide various functions to the applications 370 through the API 360 such that the applications 370 can use limited system resources within the electronic device. According to an embodiment, the middleware 330 may include at least one of a runtime library 335, an application manager 341, a window manager 342, a multi-media manager 343, a resource manager 344, a power manager 345, a database manager 346, a package manager 347, a connectivity manager 348, a notification manager 349, a location manager 350, a graphic manager 351, and a security manager 352.

The runtime library 335 may include, for example, a library module that a compiler uses in order to add a new function through a programming language while the applications 370 are being executed. The runtime library 335 may manage an input/output, manage a memory, or process an arithmetic function. The application manager 341 may manage, for example, the life cycles of the applications 370. The window manager 342 may manage GUI resources used for a screen. The multimedia manager 343 may identify a format required for reproducing media files and may perform encoding or decoding of the media files using a codec according to the format. The resource manager 344 may manage source codes of the applications 370 or a space of the memory. The power manager 345 may manage, for example, the capacity, temperature, or power of the battery, and may determine or provide information of power necessary for operations of the electronic device by using the corresponding information. According to an embodiment, the power manager 345 may operate in conjunction with a Basic Input/Output System (BIOS). The database manager 346 may create, search for, or modify a database to be used in the applications 370, for example. The package manager 347 may manage the installation or update of an application that is distributed in the form of a package file.

The connectivity manager 348 may, for example, manage wireless connection. The notification manager 349 may provide an event to the user, for example, an arrival message, an appointment, a proximity notification, and the like. The location manager 350 may manage, for example, the location information of the electronic device. The graphic manager 351 may manage, for example, a graphical effect to be provided to the user or a user interface related thereto.

The security manager 352 may provide, for example, system security or user authentication. According to an embodiment, the middleware 330 may include a telephony manager for managing a voice or video call function of the electronic device or a middleware module that is capable of forming a combination of the functions of the above-described elements. According to an embodiment, the middleware 330 may provide specialized modules according to the types of operation systems. The middleware 330 may dynamically delete some existing elements or may add new elements. The API 360 is, for example, a set of API programming functions, and may be provided with different configurations according to operating systems. For example, in the case of Android or iOS, one API set may be provided for each platform, and in the case of Tizen, two or more API sets may be provided for each platform.

The applications 370 may include a home 371, a dialer 372, an SMS/MMS 373, an instant message (IM) 374, a browser 375, a camera 376, an alarm 377, a contact 378, a voice dial 379, an email 380, a calendar 381, a media player 382, an album 383, a watch 384, healthcare (e.g., measuring the amount of exercise or blood glucose, etc.), or an environmental information (e.g., atmospheric pressure, humidity, or temperature information) providing application. According to an embodiment, the applications 370 may include an information exchange application that can support the exchange of information between the electronic device and an external electronic device. The information exchange application may include, for example, a notification relay application for transferring specific information to an external electronic device, or a device management application for managing the external electronic device. For example, a notification transfer application may transfer notification information generated by another application of the electronic device to an external electronic device, or may receive notification information from the external electronic device to provide the same to the user. The device management application may install, delete, or update, for example, a function (e.g., turning on/off an external electronic device itself (or some element parts) or adjusting brightness (or resolution) of the display) of an external electronic device communicating with the electronic device or an application operating in the external electronic device. According to an embodiment, the applications 370 may include applications (e.g., a health care application of a mobile medical appliance) that are designated according to the attributes of an external electronic device. According to an embodiment, the applications 370 may include applications received from an external electronic device. At least some of the program modules 310 may be implemented (e.g., executed) by software, firmware, hardware (e.g., the processor 210), or a combination of two or more thereof and may include a module, a program, a routine, an instruction set, or a process for performing one or more functions.

Figure 4:
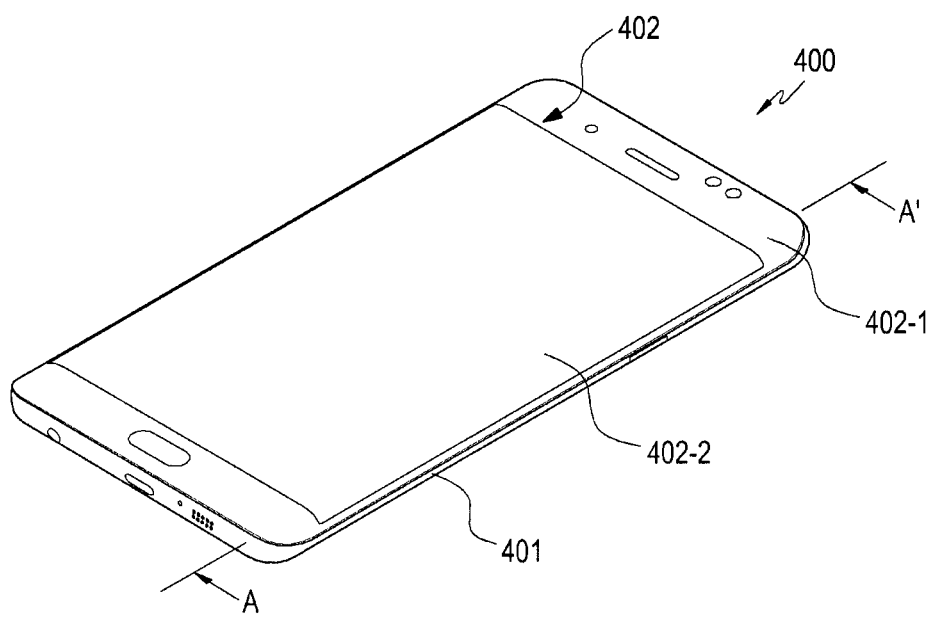
FIG. 4 is a perspective view illustrating an electronic device according to various embodiments.

FIG. 4 is a perspective view illustrating an electronic device according to various embodiments.

Referring to FIG. 4, an electronic device 400 (e.g., the electronic device 101 in FIG. 1 or the electronic device 201 in FIG. 2) may include a housing 401. According to various embodiments, the housing 401 may include a first surface facing a first direction, a second surface facing a second direction that is opposite the first direction, and a side surface surrounding at least a part of the space between the first surface and the second surface.

According to various embodiments, the housing 401 may include, for example, electronic parts as shown in FIG. 1 or FIG. 2, and a window cover 402 may be mounted on at least one surface of the housing 401. According to various embodiments, the window cover 402 may be provided on at least one of a front surface, a side surface, and a rear surface of the housing 401 of the electronic device 400. According to an embodiment, the window cover 402 may include a smart window at least in a part thereof. For example, via the window cover 402, at least one of the front surface, side surface, and rear surface of the housing 401 may include the smart window.

According to an embodiment, the window cover 402 may be provided to cover a part or all of a display (e.g., the display 160 in FIG. 1 or the display 260 in FIG. 2) and the periphery (bezel) of the display.

According to an embodiment, the window cover 402 may include a first area 402-1 and a second area 402-2. The first area 402-1 is the periphery of a screen area (active area, AA) and may be an area corresponding to a non-screen area (non-active area, NAA). The second area 402-2 may be an area corresponding to the screen area (active area, AA) on which a screen is displayed. The first area 402-1 or the second area 402-2 may include an area which can be changed via an electrical control on the basis of at least one attribute from a plurality of possible attributes. The attributes can include, for example, hue, texture, or a pattern according to electrical control For example, the area which can be changed via an electrical control on the basis of at least one attribute determined from among the plurality of attributes may include a smart window.

The window cover 402 may include at least a partial area with a changeable attribute. For example, the window cover 402 may include an attribute changing member that causes signal received by sensors to be altered. At least one processor determine control information related to the changed attributes and changes the sensitivity of the sensor. The electronic device 100 acquires peripheral information based on the changed sensitivity of the sensor.

Figure 5A:
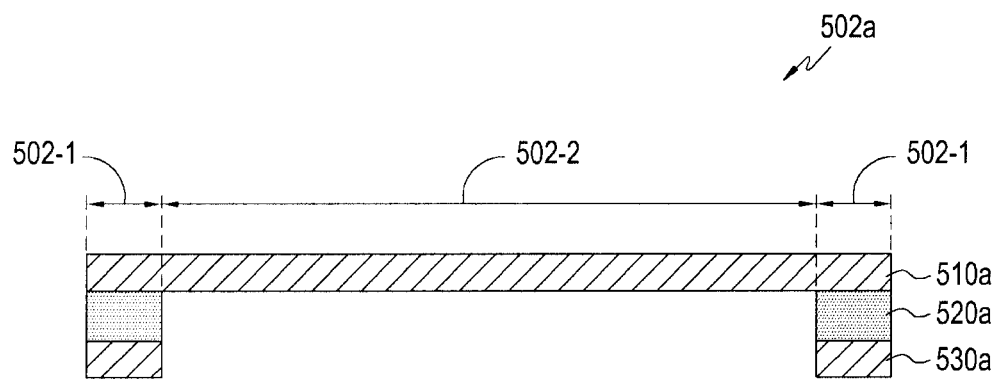
FIG. 5A and FIG. 5B are diagrams illustrating a laminated state of a window cover according to various embodiments.
Figure 5B:
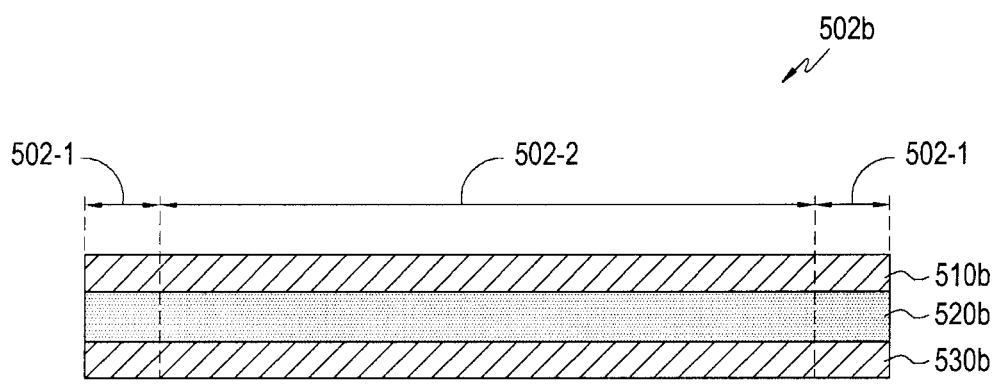

FIGS. 5A and 5B are diagrams illustrating a laminated window cover according to various embodiments. FIGS. 5A and 5B may illustrate, for example, a cross-section of the window cover 402 along line A-A.

According to various embodiments, a first area 502-1 may include a smart window (or the smart window 520 may be directly under the first area 502-1) as illustrated in FIG. 5A, or both the first area 502-1 (e.g., the first area 402-1 in FIG. 4) and a second area 502-2 (e.g., the second area 402-2 in FIG. 4) may include a smart window as illustrated in FIG. 5B (or the smart window 520 may be directly under the first area 502-1 and the second area 502-2).

Referring to FIG. 5A, when the first area 502-1 includes a smart window, the first area 502-1 may include a first member 510a and a second member 530a, an attribute changeable member 520a may be included in at least a part between the first member 510a and the second member 530a, and the second area 502-2 may include only the first member 510a.

Referring to FIG. 5B, when both the first area 502-1 and the second area 502-2 include a smart window, the first area 502-1 and the second area 502-2 may include a first member 510b, a second member 530b, and an attribute changeable member 520b that is in at least a part between the first member 510b and the second member 530b.

Referring to FIG. 5A and FIG. 5B, according to an embodiment, the first member 510a or 510b and the second member 530a or 530b may be made of glass or plastic, respectively, and may be made of a transparent material through which the interior thereof may be exposed. According to an embodiment, the attribute changeable member

520a or 520b may be a member that enables changes in attributes including at least one of a hue, a texture, or a pattern according to electronic control. For example, an area including the attribute changeable member 520a or 520b may be a smart window.

According to an embodiment, a display (e.g., the display 160 in FIG. 1 or the display 260 in FIG. 2) may be disposed below a second directional surface of the second area 502-2, and a screen of the display may be exposed. For example, the second area 502-2 may operate as a part of a touch screen in which a touch panel and a display panel are combined.

According to an embodiment, as shown in FIG. 5A, when the second area 502-2 includes only the first member 510a, a display (e.g., the display 160 in FIG. 1 or the display 260 in FIG. 2) may be disposed below the first member 510a.

According to an embodiment, as shown in FIG. 5B, when the second area 502-2 includes the first member 510b, the attribute changeable member 520b, and the second member 530b, a display (e.g., the display 160 in FIG. 1 or the display 260 in FIG. 2) may be disposed below the second member 530b. For example, when the display (e.g., the display 160 in FIG. 1 or the display 260 in FIG. 2) is disposed below the second member 530b, the attribute changeable member 520b may be controlled to be in a transparent state so that a screen of the display is exposed. For example, when a display screen is activated, the first member 510b, the attribute changeable member 520b, and the second member 530b may be in a transparent state.

According to an embodiment, the first area 502-1 is an area corresponding to the periphery of a screen area (AA) displayed by the display, and may be a bezel area. For example, terminals or signal lines including a touch panel, a display panel, etc. may be disposed below the second directional surface of the first area 502-1, the second directional surface of the first area 502-1 may be shielded by the attribute changeable member 520b in order to limit arrangement of the signal lines and terminals to be exposed to the outside. For example, the attribute changeable member may include an electrochromic material.

According to various embodiments, at least one sensor module (e.g., the sensor module 240 in FIG. 2) may be disposed below the display that is disposed below the second directional surface of the first area 502-1 or below the second directional surface of the second area 502-2. According to various embodiments, the at least one sensor module may include an optical-based sensor. According to an embodiment, the optical-based sensor may include a light reception unit that receives light, and may further include a light emission unit that outputs light. For example, the optical-based sensor may include at least one of an illuminance sensor 240K, a proximity sensor 240G an iris sensor, and a biometric sensor 240I.

According to an embodiment, the illuminance sensor may include a light reception unit and may be a sensor that senses external light through the light reception unit. For example, the illuminance sensor may be an RGB illuminance sensor 240H. The RGB illuminance sensor 240H may receive light through the light reception unit, may detect the amount of received light, and may provide a sensing result obtained by the illuminance sensor. According to an embodiment, an illuminance value may be calculated according to the sensing result obtained by the illuminance sensor. For example, on the basis of the sensing result obtained by the illuminance sensor, the amount of light in each wavelength band may be measured in R (red), G (green), B (blue) and C (clear) channels, an infrared (IR) component included in light may be removed using a value of the C channel, a type of light (e.g., incandescent lamp, halogen, etc.), i.e., a light source, may be distinguished via a ratio of each channel, and an illuminance value may be calculated according to an equation specific to each light source. For example, the equation specific to each light source may be determined in advance for each illuminance sensor manufacturer.

According to an embodiment, the proximity sensor 240G may include a light reception unit and a light emission unit (e.g., light emitting diode (LED)), wherein the proximity sensor outputs light through the light emission unit, and measures the amount of light reflected by a target object and returning to the light reception unit, so as to measure the presence or absence of an external object exists and the proximity of the external object.

According to an embodiment, the iris sensor may include a light emission unit (e.g., infrared ray light emitting diode (IR LED)) and a camera that functions to receive light, wherein the iris sensor outputs light through the light emission unit, acquires an image through the camera that receives reflected light, and recognizes an iris from the acquired image. In the iris sensor, the light emission unit and the camera may be spaced apart from each other by a predetermined interval in order to recognize an accurate iris shape. For example, the iris sensor may perform iris recognition by: receiving light emitted from the light emission unit (e.g., an IR LED) to acquire an image, by a camera module (e.g., an IR camera module); selecting an image suitable for iris recognition through preprocessing of the acquired image; improving the selected image to an image appropriate for iris recognition and then extracting an iris area therefrom; and extracting a uniquely coded binary value from an extracted iris image and then performing comparison with a previously stored iris image, thereby determining whether the comparison shows a match.

According to an embodiment, the biometric sensor 240I may include a light emission unit and a light reception unit, and may be a sensor that outputs light to a living body through the light emission unit and receives light reflected by the living body through the light reception unit so as to acquire biometric information. For example, the biometric sensor may include a heart rate sensor (capable of measuring heart rate, stress, and oxygen saturation), a fingerprint sensor, a blood glucose sensor, a blood pressure sensor, and the like.

According to various embodiments, at least one optical sensors may be disposed in various positions within the housing 401 of the electronic device so as to sense light, and may perform various sensing operations by using the sensed light.

According to an embodiment, when an optical-based sensor is disposed around a structure that may affect light sensing among various positions in the electronic device, the optical-based sensor may have difficulty in performing an accurate sensing operation due to the structure affecting light sensing of the optical-based sensor. For example, the structure that may affect light sensing of the optical-based sensor may be a smart window having attributes, such as a color, a texture, or a pattern, which may be changed by an electrical signal, or may be a display in which a displayed color or brightness may be changed.

For example, when the optical-based sensor is disposed around the smart window of the first area 502-1, light corresponding to a color, a texture, and a pattern, which change as attributes such as a color, a texture, or a pattern of the smart window change, may affect a sensitivity of the optical-based sensor, and therefore the sensitivity of the optical-based sensor may need to be adjusted. Further, when the optical-based sensor is disposed around the display of the second area 502-2, light corresponding to a display color and brightness, which change as attributes such as a color or brightness of the display change, may affect sensitivity of the optical-based sensor, and therefore the sensitivity of the optical-based sensor may need to be adjusted.

According to various embodiments, an electronic device may include: a housing; a window cover housed in the housing, wherein an attribute of at least a partial area of a window cover may be changed via an electrical control; at least one sensor disposed below at least the partial area; and at least one processor, wherein the at least one processor is configured to identify control information related to an operation of changing the attribute of at least the partial area of the window cover, to determine a sensitivity related to the at least one sensor corresponding to information on the at least one attribute at least on the basis of the control information, and to acquire peripheral information of the exterior of the electronic device by using the at least one sensor, at least on the basis of the determined sensitivity.

According to an embodiment, the at least one sensor may include a light reception module, and the at least one processor may be configured to adjust at least one setting value related to the light reception module at least on the basis of the determined control information. For example, the at least one setting value related to the light reception module may include an illuminance coefficient.

According to an embodiment, the at least one sensor may include a light emission module for outputting light, and a light reception module for receiving the light after being reflected by an external object, and the at least one processor is configured to determine, as at least a part of the operation for acquiring the peripheral information, a proximity of the external object at least on the basis of sensing of the reflected light by using the light reception module. For example, the at least one processor may be configured to determine at least one condition for determining the proximity, at least on the basis of the control information. Frequency example, in order to determine the proximity, the at least one condition may include a recognition threshold value or a release threshold value.

According to an embodiment, the at least one sensor may include a light emission module for outputting light, and a camera module that receives the light after being reflected by an external object to acquire an image, and the at least one processor may be configured to recognize, as at least a part of the operation for acquiring the peripheral information, an iris from the acquired image at least on the basis of sensing of the reflected light by using the camera module. According to an embodiment, the at least one processor may be configured to determine at least one condition for recognizing the iris, on the basis of the control information. For example, the at least one condition for recognizing the iris may include a current, a light emission unit output time (pulse length), a light reception time (integration time).

According to an embodiment, the at least one processor may be configured to change, as at least a part of the operation for changing the attribute to the at least one attribute, at least one of a color, a texture, and a pattern of at least the partial area.

According to an embodiment, the electronic device may further include a memory that stores one or more setting values according to a light transmissivity of at least the partial area, and the at least one processor may be configured to, as at least a part of the operation for determining the sensitivity, identify a light transmissivity of at least the partial area, which corresponds to the at least one attribute, and to adjust setting of the at least one sensor on the basis of at least one setting value corresponding to the light transmissivity among the one or more setting values in the memory.

According to an embodiment, the at least one processor may be configured to correct, as at least a part of the operation for acquiring peripheral information of the exterior of the electronic device, a sensing value acquired using the at least one sensor, at least on the basis of the sensitivity.

Figure 6:
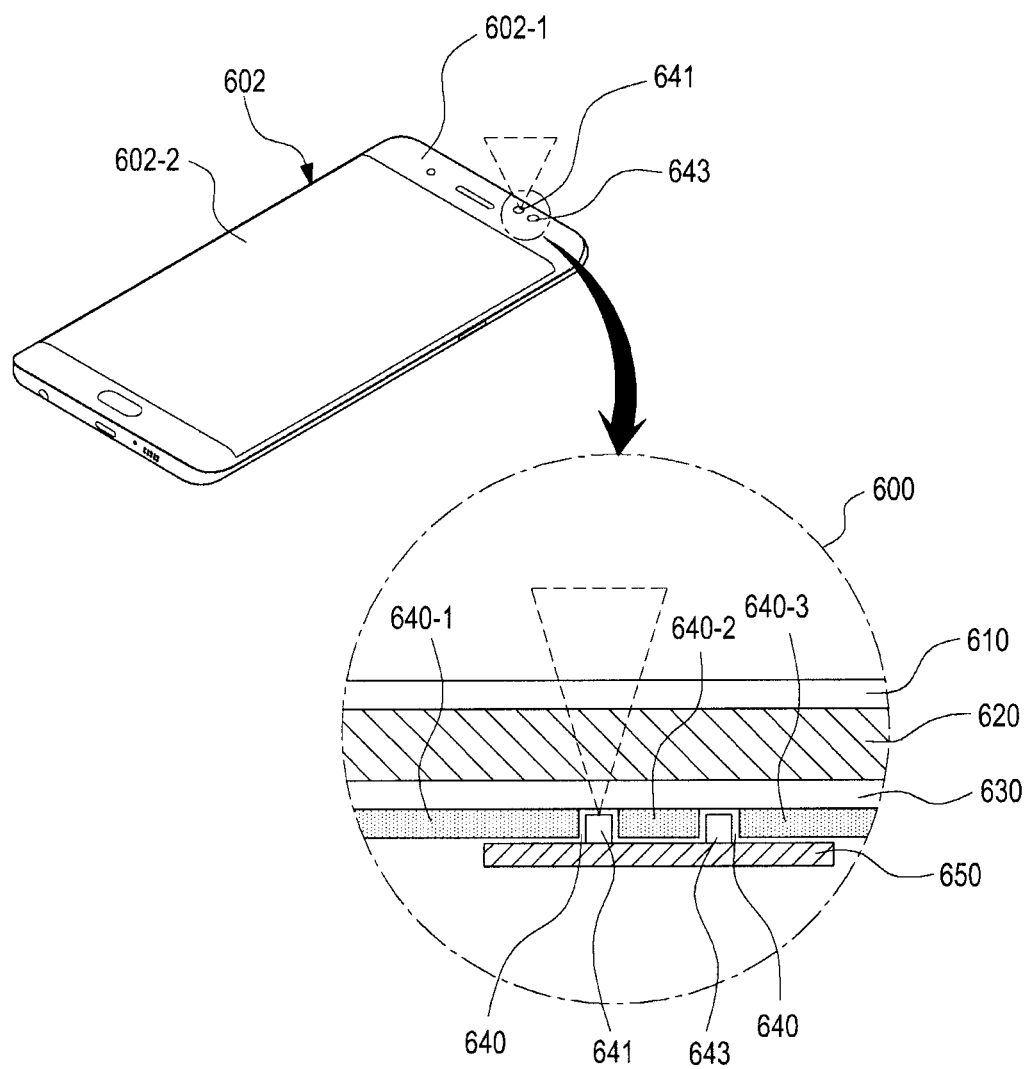
FIG. 6 is a diagram illustrating an example in which at least one sensor is disposed below at least a partial area of a window cover according to various embodiments.

FIG. 6 is a diagram illustrating an example in which at least one sensor is disposed below at least a partial area of a window cover according to various embodiments.

Referring to FIG. 6, a window cover 602 (e.g., reference numeral 402 in FIG. 4, 502a in FIG. 5A, or 502b in FIG. 5B) may include a first area 602-1 and a second area 602-2. The first area 602-1 is the periphery of a screen area (active area, AA) and may be an area corresponding to a non-screen area (non-active area, NAA). The second area 602-2 may be an area corresponding to the screen area (active area, AA) on which a screen is displayed. The first area 602-1 or the second area 602-2 may include an area which can be changed via an electrical control on the basis of at least one attribute determined from among a plurality of attributes. For example, the area which can be changed via an electrical control on the basis of at least one attribute determined from among the plurality of attributes may include a smart window.

According to an embodiment, a cross-section 600 is a part of the first area 602-1 (e.g., reference numeral 402-1 in FIG. 4 or 502-1 in FIGS. 5A and 5B), and may have one or more sensor members 641 and 643 disposed thereon. According to various embodiments, the one or more sensor members 641 and 643 may include at least one of an illuminance sensor, a proximity sensor, an iris sensor, and a biometric sensor.

According to various embodiments, the first area 602-1 may include a smart window including a first plate member 610 (e.g., the first member 510a in FIG. 5A or the first member 510b in FIG. 5B), an electrochromic (ECC) area 620 (e.g., the attribute changeable member 520a in FIG. 5A or the attribute changeable member 520b in FIG. 5B), and a second plate member 630 (e.g., the second member 530a in FIG. 5A or the second member 530b in FIG. 5B), wherein one or more sensor modules 641 and 643, structures 640-1 to 643-3 forming one or more openings 640 for securing a mounting space of the one or more sensor members 641 and 643, and a circuit board 650 may be disposed below the second plate member 630.

The first plate member 610 may be a transparent member attached on the uppermost surface in a first direction of the window cover 602, and may be made of glass or plastic. An electrochromic area 620 may be included between the first plate member 610 and the second plate member 630. The electrochromic area 620 may include an electrochromic material having attributes, some of which are changeable, and an electrode connected to the electrochromic material. In the electrochromic area 620, at least one attribute thereof may be changed due to occurrence of a chemical reaction caused by a current flowing in the electrode. For example, the at least one attribute may be at least one of a color, a texture, or a pattern. The structures 640-1 to 643-3 forming one or more openings 640 for securing a mounting space of the one or more sensor members 641 and 643 may be disposed below the second plate member 630. The one or more sensor members 641 and 643 may be seated in the one or more openings 640, respectively. According to various embodiments, at least a part of sensor members among the one or more sensor modules may be seated in a single opening, or at least parts of sensor members of the multiple sensor modules may be seated in the multiple openings, respectively. The at least a part of the sensor members may include a light reception unit or a light emission unit. For example, the first sensor member 641 may be a light emission unit, the second sensor member 643 may be a light reception unit, and the light emission unit and the light reception unit may be seated in two openings, respectively. Although not illustrated, the first sensor member 641 and the second sensor member 643 may be seated in a single opening.

The circuit board 650 may be disposed below the bottom surfaces of the one or more sensor members 641 and 643. For example, the circuit board 650 may include a printed circuit board (PCB).

In certain embodiments, due to changes in the electrochromic area (ECC) 620, the light transmission properties of the window cover 602 may change, causing changes in the light that is incident upon the sensors 641 and 643. At least one processor identifies control information for the changed light transmission properties and determines a sensitivity for the sensors based on the control information.

Figure 7A:
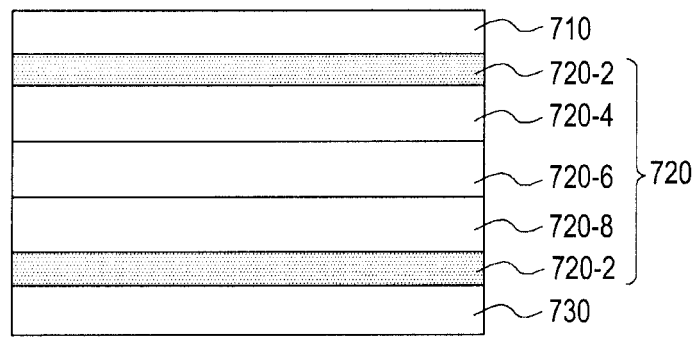
FIG. 7A, FIG. 7B and FIG. 7C are diagrams for describing an operation of a smart window according to various embodiments.
Figure 7B:
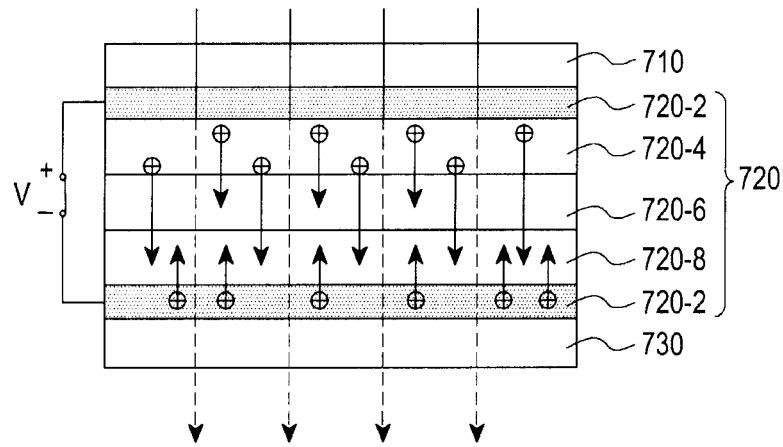
Figure 7C:
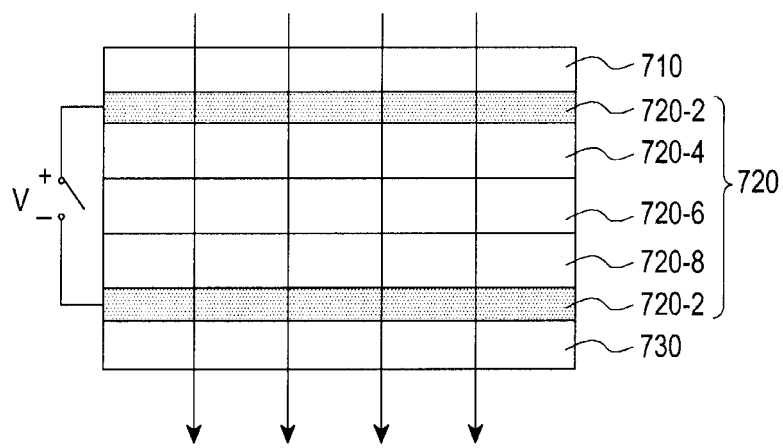

FIGS. 7A to 7C are diagrams for describing an operation of a smart window according to various embodiments.

Referring to FIG. 7A, a smart window may be a part including an electrochromic (ECC) area 720 (e.g., the electrochromic area 620 in FIG. 6) between a first plate member 710 (e.g., the first plate member 610 in FIG. 6) and a second plate member 730 (e.g., the second plate member 630 in FIG. 6). The ECC area 720 may include first and second transparent electrodes or indium tin oxide (ITO) 720-2, an ion storage layer 720-4, an ion conductor and electrolyte 720-6, and an electrochromic (ECC) layer 720-8.

Referring to FIG. 7B, when the first and second transparent electrodes 720-2 are turned on and voltages are applied to the first and second transparent electrodes 720-2, ions move to the ECC layer 720-8 through the ion conductor and electrolyte 720-6 in the ion storage layer 720-4, the moving ions absorb light, and therefore attributes, such as a color, a texture, or a pattern, of the ECC area 720 may change. For example, movement attributes of the ions may change according to the magnitude of the voltages applied to the first and second transparent electrodes 720-2, and the attributes, such as a color, a texture, or a pattern, of the ECC area 720 may change accordingly. As the attributes, such as a color, a texture, or a pattern, of the ECC area 720 change, a transmissivity of light outside the smart window, which transmits through the smart window may vary.

Referring to FIG. 7C, when the first and second transparent electrodes 720-2 are turned off and voltages are not applied to the first and second transparent electrodes 720-2, the ions having moved to the ECC layer 720-8 may return to the ion storage layer 720-2 through the ion conductor and electrolyte 720-6, and the attributes, such as a color, a texture, or a pattern, having changed according thereto may return to their original state accordingly. For example, the original state may be a transparent state. As the attributes, such as a color, a texture, or a pattern, of the ECC area 720 change to the original state, the transmissivity of light outside the smart window, which transmits through the smart window may return to the original state.

Figure 8:
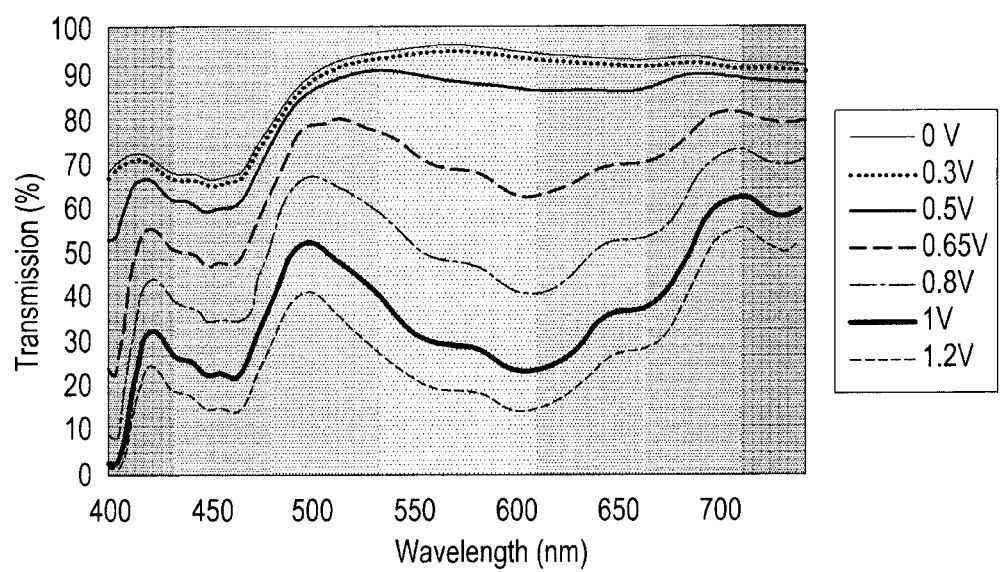
FIG. 8 is a diagram illustrating a wavelength-specific transmissivity according to a color of an ECC area according to various embodiments.

FIG. 8 illustrates the transmission percentage of different wavelengths for different voltage levels. In general, the higher the voltage level, the lower the transmission percentage.

Referring to FIG. 8, a horizontal axis represents a wavelength, and a vertical axis represents a transmissivity (%).

According to an embodiment, a color of an ECC area (e.g., the ECC area 620 in FIG. 6 or the ECC area 720 in FIG. 7) may change according to the magnitude of voltages applied to the ECC area. For example, the ECC area may become yellow when the voltage applied to the ECC area is about 0 V, the ECC area may become orange when the voltage applied to the ECC area is about 0.3 V, the ECC area may become red when the voltage applied to the ECC area is about 0.5 V, the ECC area may become blue when the voltage applied to the ECC area is about 0.65 V, the ECC area may become purple when the voltage applied to the ECC area is about 0.8 V, the ECC area may become light blue when the voltage applied to the ECC area is about 1V, and the ECC area may become green when the voltage applied to the ECC area is about 1.2V.

According to an embodiment, a wavelength-specific transmissivity may vary according to the color of the ECC area. For example, a wavelength-specific transmissivity according to a color of the ECC area may be high in the order of yellow, orange, red, blue, purple, light blue, and green. For example, a wavelength-specific transmissivity of a case when the ECC area is yellow may be higher than a wavelength-specific transmissivity of a case when the ECC area is orange, red, blue, purple, light blue, or green.

According to various embodiments, when one or more sensor modules (e.g., reference numerals 641 and 643 in FIG. 6), for example, an optical-based sensor, are disposed below a first area (e.g., reference numeral 402-1 in FIG. 4, 502-1 in FIGS. 5A and 5B, or 602-1 in FIG. 6), a change in the wavelength-specific transmissivity of the first area in accordance with a change in attributes, such as a color, a texture, or a pattern, of an electrochromic (ECC) area (e.g., reference numeral 620 in FIG. 6 or 720 in FIG. 7) may affect the optical-based sensor. Although a change in the wavelength-specific transmissivity of the first area in accordance with a change in attributes, such as a color, a texture, or a pattern, of the first area affects the optical-based sensor, if a sensitivity of the optical-based sensor is kept fixed, accuracy of a sensing performance of the optical-based sensor may be lowered. According to various embodiments, the optical-based sensor may include at least one of an illuminance sensor, a proximity sensor, an iris sensor, and a biometric sensor.

For example, when the illuminance sensor is disposed below the first area (e.g., reference numeral 402-1 in FIG. 4, 502-1 in FIGS. 5A and 5B, or 602-1 in FIG. 6), light incident on the illuminance sensor may change according to a transmissivity change of the first area, which is caused in accordance with a change in attributes, such as a color, a texture, or a pattern, of the first area, and accuracy of the illuminance sensor may be lowered, so that acquisition of accurate illuminance information may fail. When the illuminance information is not accurate, a function of using the illuminance information, for example, a function of controlling brightness of a display screen according to the illuminance information may cause a malfunction.

In addition, when the proximity sensor is disposed below the first area (e.g., reference numeral 402-1 in FIG. 4, 502-1 in FIGS. 5A and 5B, or 602-1 in FIG. 6), light incident on the proximity sensor may change according to a transmissivity change of the first area, which is caused in accordance with a change in attributes, such as a color, a texture, or a pattern, of the first area, and accuracy of the proximity sensor may be lowered, so that acquisition of accurate proximity information may fail. When the proximity information is not accurate, a function of using proximity detection information by the proximity sensor, for example, a function of detecting a busy state on the basis of the proximity information and deactivating touch sensing may cause a malfunction.

Further, when the iris sensor is disposed below the first area (e.g., reference numeral 402-1 in FIG. 4, 502-1 in FIGS. 5A and 5B, or 602-1 in FIG. 6), light incident on the iris sensor may change according to a transmissivity change of the first area, which is caused in accordance with a change in attributes, such as a color, a texture, or a pattern, of the first area, and an accurate iris recognition distance and a release distance for iris recognition may not be derived. When the accurate iris recognition distance and the release distance are unable to be derived, a user may have inconvenience relating to iris recognition.

According to various embodiments, in the case of an optical-based sensor disposed below the first area (e.g., reference numeral 402-1 in FIG. 4, 502-1 in FIGS. 5A and 5B, or 602-1 in FIG. 6), a sensitivity of the optical-based sensor may be determined on the basis of a change in the wavelength-specific transmissivity of the first area, which is caused in accordance with a change in attributes, such as a color, a texture, or a pattern, of the electrochromic (ECC) area 720, and the optical-based sensor may be operated according to the determined sensitivity.

According to various embodiments, in the case of an optical-based sensor disposed below the first area (e.g., reference numeral 402-1 in FIG. 4, 502-1 in FIGS. 5A and 5B, or 602-1 in FIG. 6), a sensing value obtained by the optical-based sensor may be adjusted on the basis of a change in the wavelength-specific transmissivity of the first area, which is caused in accordance with a change in attributes, such as a color, a texture, or a pattern, of the electrochromic (ECC) area 720 (e.g., reference numeral 620 in FIG. 6 or 720 in FIG. 7).

For example, when the applied voltage is 0.5 V, the ECC area 720 may have a lower transmission percentage for red light. Accordingly, the at least one processor can adjust the sensitivity of the RGB sensor to have higher sensitivity to red light. According to various embodiments, an electronic device may include a display, at least one sensor disposed below at least a partial area of the display, and at least one processor, wherein the at least one processor is configured to identify control information related to displaying of at least the partial area of the display, to determine a sensitivity related to the at least one sensor at least on the basis of the control information, and to acquire peripheral information of the exterior of the electronic device by using the at least one sensor, at least on the basis of the determined sensitivity.

According to an embodiment, in the electronic device, the at least one sensor may include a light reception module, and the at least one processor may be configured to adjust a setting value related to the light reception module at least on the basis of the control information.

According to an embodiment, the at least one sensor may include a light emission module for outputting light, and a light reception module for receiving the light after being reflected by an external object, and the at least one processor may be configured to determine, as at least a part of the operation for acquiring the peripheral information, a proximity of the external object at least on the basis of sensing of the reflected light by using the light reception module.

According to an embodiment, the at least one processor may be configured to determine at least one condition for determining the proximity, at least on the basis of the control information.

According to an embodiment, the at least one sensor may include a light emission module for outputting light, and a camera module that receives the light after being reflected by an external object to acquire an image, and the at least one processor may be configured to recognize, as at least a part of the operation for acquiring the peripheral information, an iris from the acquired image at least on the basis of sensing of the reflected light by using the camera module.

According to an embodiment, the at least one processor may be configured to determine at least one condition for recognizing the iris, at least on the basis of the control information.

According to an embodiment, the at least one processor may be configured to identify, as at least a part of the operation for identifying the control information, at least one of brightness control information and color control information relating to displaying of at least the partial area.

According to an embodiment, the electronic device may further include a memory that stores one or more setting values according to a light transmissivity of at least the partial area, and the at least one processor may be configured to, as at least a part of the operation for determining the sensitivity, identify a light transmissivity of at least the partial area, and to adjust setting of the at least one sensor on the basis of at least one setting value corresponding to the light transmissivity among the one or more setting values in the memory, at least on the basis of the color control information or the brightness control information.

According to an embodiment, the processor may be configured to correct, as at least a part of the operation for acquiring peripheral information of the exterior of the electronic device, a sensing value acquired using the at least one sensor, at least on the basis of the sensitivity.

Figure 9:
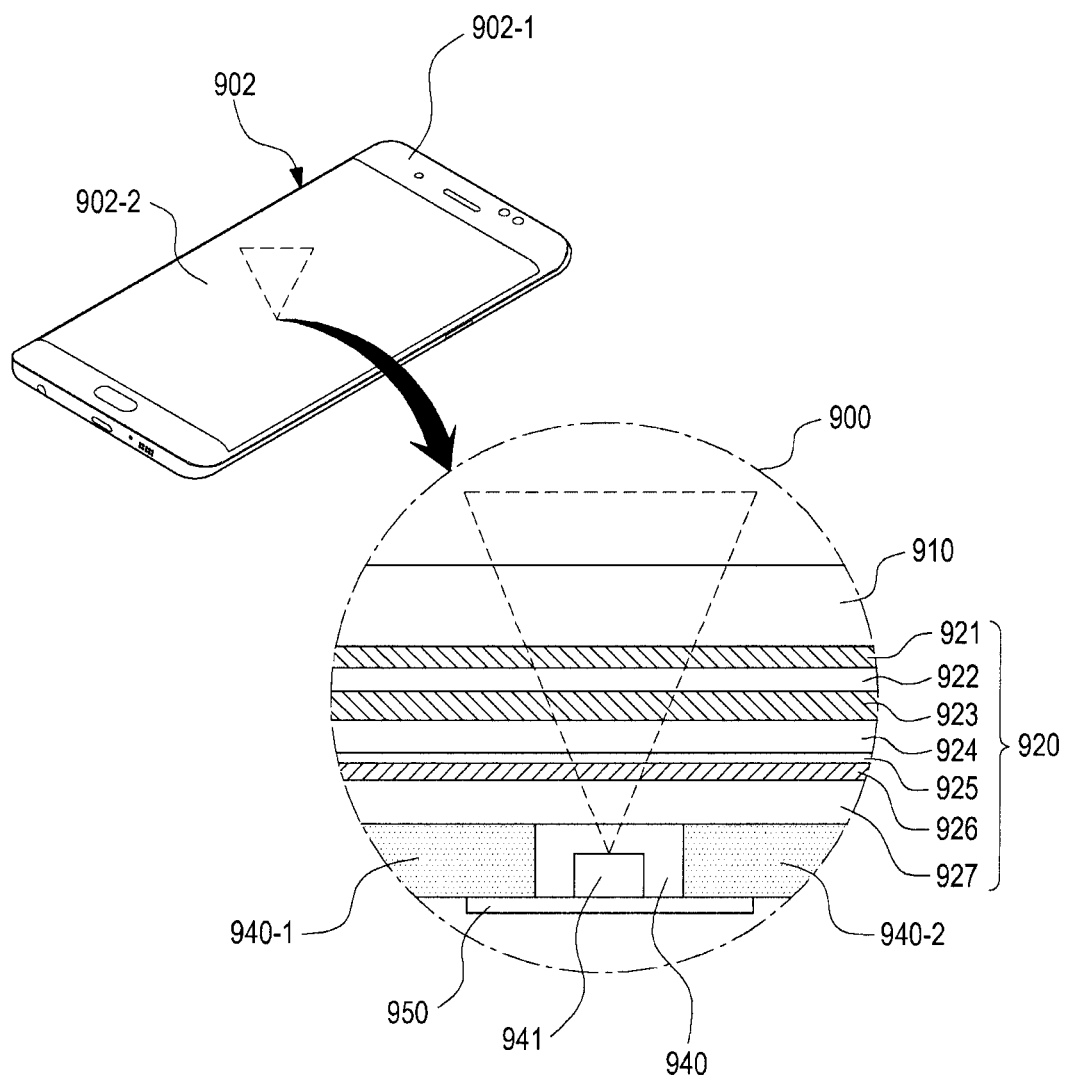
FIG. 9 is a diagram illustrating an example in which at least one sensor is disposed below at least a partial area of a display according to various embodiments.

FIG. 9 is a diagram illustrating an example in which at least one sensor is disposed below at least a partial area of a display according to various embodiments.

Referring to FIG. 9, a window cover 902 (e.g., reference numeral 402 in FIG. 4, 502a in FIG. 5A, or 502b in FIG. 5B) may include a first area 902-1 and a second area 902-2. The first area 902-1 is the periphery of a screen area (active area, AA) and may be an area corresponding to a non-screen area (non-active area, NAA). The second area 902-2 may be an area corresponding to the screen area (active area, AA) on which a screen is displayed. The first area 902-1 or the second area 902-2 may include an area which can be changed via an electrical control on the basis of at least one attribute determined from among a plurality of attributes. For example, the area which can be changed via an electrical control on the basis of at least one attribute determined from among the plurality of attributes may include a smart window.

According to an embodiment, a cross-section 900 is a part of the second area 902-2 of the window cover 902, and may be a cross-section of a part on which one or more sensor members 941 is disposed. According to various embodiments, the one or more sensor members 941 may include an illuminance sensor, a proximity sensor, an iris sensor, and a biometric sensor.

According to various embodiments, the second area 902-2 may include a first plate member 910, wherein a display 920 (e.g., reference numeral 160 in FIG. 1 or 260 in FIG. 2) is disposed below the first plate member 910, and the one or more sensor members 941 (e.g., reference numeral 240 in FIG. 2), structures 940-1 and 940-2 forming one or more openings 940 for securing a mounting space of the one or more sensor members 941, and a circuit board 950 may be disposed below the display 920.

According to various embodiments, the first plate member 910 may be installed on the uppermost surface in a first direction of the window cover 902, may be made of a transparent material capable of protecting the display 920, and may be made of glass or plastic. The display 920 may be disposed below the first plate member 910.

According to various embodiments, the display 920 may include, between a first surface and a second surface of the display 920, a first optically clear adhesive (OCA) film 921, a touch panel 922, a second optically clear adhesive film 923, an OLED layer (a polarizing panel 924 and a display panel 925), a first polymer layer 926, and a second polymer layer 927, which may be stacked in order.

The touch panel 922 (e.g., the touch panel 252 in FIG. 2) may be an element provided so as to enable implementation of input according to a touch on the screen area (AA) or a proximity thereto. According to various embodiments, the touch panel 922 may be implemented in various types, such as a capacitive type touch panel, an electromagnetic resonance type touch panel, a resistive type touch panel, an infrared type touch panel, an electromagnetic resonance (EMR) type touch panel, or an acoustic wave type touch panel, and may be implemented by a combination thereof. The touch panel 922 may be disposed over the surface of the display 920 described above, for example, between the first plate member 910 and the OLED layer (the polarizing panel 924 and the display panel 925).

According to various embodiments, the first and second optically clear adhesive (OCA) films 921 and 923 may be provided to couple between the first plate member 910 and the touch panel 922 and to couple between the touch panel 922 and the polarizing plate 924, respectively. Further, the first and second optically clear adhesive films 921 and 923 may be provided not only to couple the touch panel 922 and the polarizing panel 924, but also to transmit an electrical signal between the polarizing panel 924, the first polymer layer 926 such as polyimide, and the touch panel 922.

According to various embodiments, the second polymer layer 927 may form a second surface of the display 920. The second polymer layer 927 may be provided below the bottom surface of the first polymer layer 926, and when the first polymer layer 926 is formed thin, a transparent support polymer panel (polyethylene terephthalate (PET)) may be provided to support and reinforce the first polymer layer 926.

According to various embodiments, the first polymer layer 926 may be a polyimide film. Further, the first polymer layer 926 is an element to supply power to the display panel 925, and may be provided to be electrically combined with a printed circuit board 950 (e.g., a flexible printed circuit board (FPCB)) and to be connected with a main circuit board mounted inside a housing (e.g., reference numeral 401 in FIG. 4).

The OLED layer (the polarizing panel 924 and the display panel 925) may contact the first polymer layer 926, and may be disposed between the first polymer layer 926 and the first surface of the display 920. The polarizing panel 924 is laminated below the bottom surface of the second optically clear adhesive film 923, and may be provided to improve a picture quality of a screen of the display panel 925 and to improve outdoor visibility. According to various embodiments, the OLED layer has been taken as an example for a layer for displaying a screen, but the present disclosure is not limited thereto.

According to various embodiments, below the bottom surface of the display 920, the structures 940-1 and 940-2 forming the opening 940 are disposed so that one or more sensor members 941 may be seated at a predetermined position below the display 920, the one or more sensor members 941 may be seated in the opening 940, and the circuit board 950 electrically connected to the one or more sensor members 941 may be disposed. For example, a first sensor member 941 may include a light emission unit or may include a light emission unit and a light reception unit, wherein the light emission unit or the light emission unit and light reception unit may be seated in a single opening.

According to various embodiments, when one or more sensor modules (e.g., reference numeral 941 in FIG. 9), for example, an optical-based sensor, are disposed below a display (e.g., reference numeral 920 in FIG. 9) of a second area (e.g., reference numeral 402-2 in FIG. 4, 502-2 in FIGS. 5A and 5B, 602-2 in FIG. 6, or 902-2 in FIG. 9), a color or brightness of a display screen may affect the optical-based sensor as attributes, such as a color or brightness, of a display area that are displayed by the display 920 change. Although a change in the color or brightness of the display screen affects the optical-based sensor, if a sensitivity of the optical-based sensor is kept fixed, accuracy of a sensing performance of the optical-based sensor may be lowered.

According to various embodiments, in the case of an optical-based sensor disposed below a display (e.g., reference numeral 920 in FIG. 9) of a second area (e.g., reference numeral 402-2 in FIG. 4, 502-2 in FIGS. 5A and 5B, 602-2 in FIG. 6, or 902-2 in FIG. 9), a sensitivity of the optical-based sensor may be adjusted on the basis of a change in a color or brightness of a display screen and the optical-based sensor may be controlled to operate according to the adjusted sensitivity.

According to various embodiments, in the case of an optical-based sensor disposed below a display (e.g., reference numeral 920 in FIG. 9) of a second area (e.g., reference numeral 402-2 in FIG. 4, 502-2 in FIGS. 5A and 5B, 602-2 in FIG. 6, or 902-2 in FIG. 9), a sensing value obtained by the optical-based sensor may be adjusted on the basis of a change in a color or brightness of a display screen.

Figure 10:
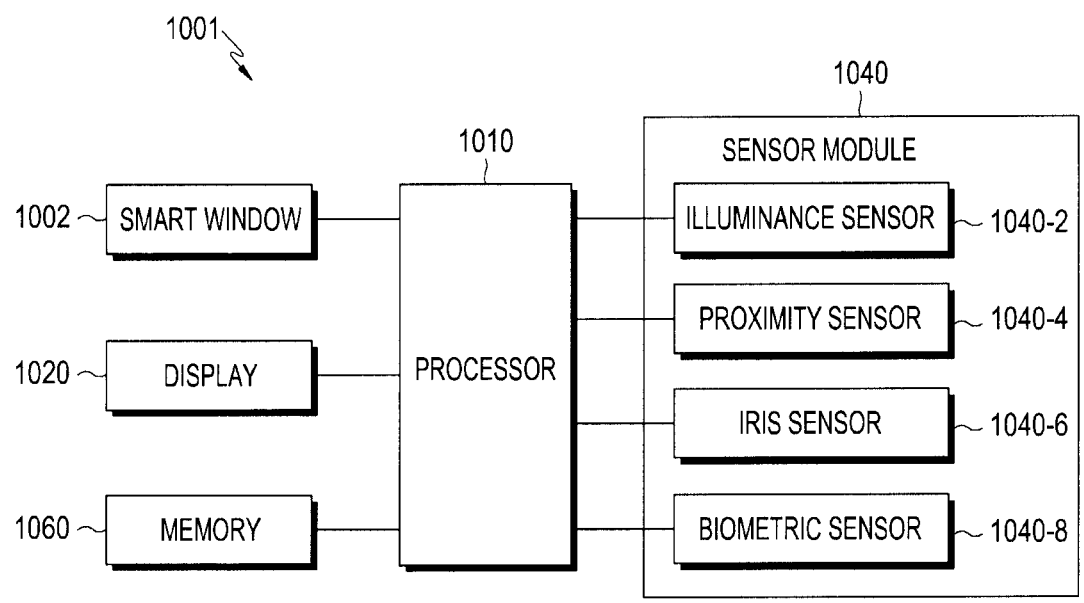
FIG. 10 is a configuration diagram of an electronic device according to various embodiments.

FIG. 10 is a configuration diagram of an electronic device according to various embodiments.

Referring to FIG. 10, an electronic device 1001 according to an embodiment may include one or both of the electronic device 101 illustrated in FIG. 1 and the electronic device 201 illustrated in FIG. 2, and may include a smart window 1002, a processor 1010, a display 1020, a sensor module 1040, a memory 1060.

In the smart window 1002, at least a partial area may be changed via an electrical control on the basis of at least one determined attribute among a plurality of attributes. According to an embodiment, the smart window 1002 may be included in at least a partial area of a window cover (e.g., reference numeral 402 in FIG. 4, 502a in FIG. 5A, 502b in FIG. 5B, 602 in FIG. 6, or 902 in FIG. 9), for example, a first area (e.g., reference numeral 402-1 in FIG. 4, 502-1 in FIG. 5A and FIG. 5B, 602-1 in FIG. 6, or 902-1 in FIG. 9), may be included in both the first area and a second area (e.g., reference numeral 402-2 in FIG. 4, 502-2 in FIG. 5A and FIG. 5B, 602-2 in FIG. 6, or 902-2 in FIG. 9), or may be included in another part of the electronic device 1001 excluding the window cover. The smart window 1002 may be changed via an electrical control on the basis of at least one attribute determined from among a plurality of attributes.

The processor 1010 may include one or more processors. The processor 1010 may include one or both of the processor 120 illustrated in FIG. 1 and the processor 210 illustrated in FIG. 2. The processor 1010 may perform data processing or operations relating to control and/or communication of one or more other elements of the electronic device 1001. The processor 1010 may drive, for example, an operating system or application programs to control a plurality of hardware or software elements connected thereto and may perform various types of data processing and operations.

According to various embodiments, the processor 1010 may be a low power processor, such as an application processor (AP) or a sensor hub, or may include both thereof.

According to various embodiments, the processor 1010 may transfer, to the smart window 1002, control information for controlling at least one attribute of the smart window 1002 on the basis of a user input, a function to be executed, an application type, or the like. According to an embodiment, the processor 1010 may include a smart window processor and may control the smart window 1002 through the smart window processor. According to an embodiment, the control information for controlling at least one attribute of the smart window 1002 may include control information for changing at least one among a color, a texture, and a pattern of the smart window 1002. The smart window 1002 may have at least one attribute among the color, texture, and pattern thereof, which may be changed on the basis of the control information. According to an embodiment, the control information for changing at least one attribute among the color, texture, and pattern of the smart window 1002 may be stored in a memory 1060.

The processor 1010 may transfer, to the display 1020, control information for controlling displaying of at least a partial area of the display 1020 on the basis of a user input, a function to be executed, an application type, or the like. According to an embodiment, the control information relating to displaying of at least the partial area of the display 1020 may include at least one among a color setting value for controlling a color of at least the partial area of the display 1020 and a brightness setting value for controlling brightness of at least the partial area of the display 1020. The control information for controlling displaying of at least the partial area of the display 1020 may be stored in the memory 1060.

According to various embodiments, control information (hereinafter, also referred to as "first control information") corresponding to attributes of the smart window 1002 may be identified, or control information (hereinafter, also referred to as "second control information") relating to displaying of at least a partial area of a display area of the display 1020 may be identified.

According to an embodiment, the processor 1010 may identify first control information corresponding to attributes of an attribute changeable member (e.g., reference numeral 520a in FIG. 5A, 520b in FIG. 5B, 620 in FIG. 6, or 720 in FIG. 7) included in the smart window 1002. For example, the attributes of the attribute changeable member may be at least one attribute among a color, a texture, and a pattern. According to an embodiment, the attribute changeable member may include an electrochromic area (reference numeral 620 in FIG. 6 or 720 in FIG. 7). According to an embodiment, the first control information may be associated with a sensitivity relating to at least one sensor disposed below at least a partial area of the smart window 1002, and stored in the memory 1060.

According to an embodiment, the processor 1010 may identify second control information corresponding to attributes of a screen displayed on the display 1020. For example, the attributes of the screen displayed on the display 1020 may be a color, brightness, etc. of the screen. According to various embodiments, each of the first control information and the second control information may be stored in a memory 1060.

The processor 1010 may determine a sensitivity related to at least one sensor disposed below the smart window 1002 on the basis of the first control information, or may determine a sensitivity relating to at least one sensor disposed below the display 1020 on the basis of the second control information. According to an embodiment, the first control information may be associated with the sensitivity related to at least one sensor disposed below the smart window 1002 and stored in the memory 1060, and the second control information may be associated with the sensitivity related to at least one sensor disposed below at least a partial area of a display area of the display 1020 and stored in the memory 1060.

The processor 1010 may perform control to acquire peripheral information of the exterior of the electronic device 1001 by using at least one sensor disposed below the smart window 1002, at least on the basis of the sensitivity determined on the basis of the first control information. Further, the processor 1010 may perform control to acquire the peripheral information of the exterior of the electronic device 1001 by using at least one sensor disposed below at least the partial area of the display area of the display 1020, at least on the basis of the sensitivity determined on the basis of the second control information.

The sensor module 1040 (e.g., the sensor module 240 in FIG. 2) may include at least one sensor. The at least one sensor may be at least one among an illuminance sensor 1040-2 (e.g., the illuminance sensor 240K in FIG. 2), a proximity sensor 1040-4 (e.g., the proximity sensor 240G in FIG. 2), an iris sensor 1040-6, and a biometric sensor 1040-8 (e.g., the biometric sensor 240I in FIG. 2). The at least one sensor may be disposed below the smart window 1002 or may be disposed below at least the partial area of the display area of the display 1020.

According to an embodiment, the illuminance sensor 1040-2 may include a light reception unit and may be a sensor that senses external light through the light reception unit. For example, the illuminance sensor 1040-2 may be an RGB illuminance sensor. The RGB illuminance sensor may receive light through the light reception unit, may detect the amount of received light, and may provide a sensing result to the processor 1010. On the basis of the sensing result obtained by the illuminance sensor 1040-2, the processor 1010 may measure the amount of light in each wavelength band in R (red), G (green), B (blue) and C (clear) channels, may remove an infrared (IR) component included in light by using a value of the C channel, may distinguish a type of light (e.g., incandescent lamp, halogen, etc.), i.e., a light source, via a ratio of each channel, and may calculate an illuminance value according to an equation specific to each light source. For example, the equation specific to each light source may be determined in advance for each illuminance sensor manufacturer.

According to an embodiment, the proximity sensor 1040-4 may include a light reception unit and a light emission unit (e.g., LED), wherein the proximity sensor outputs light through the light emission unit, detects the amount of light reflected by a target object and returning to the light reception unit, and transfers the detected amount of light to the processor 1010. The processor 1010 may measure the presence or absence of an external object exists and the proximity of the external object, by using a detection result obtained by the proximity sensor 1040-4.

According to an embodiment, the iris sensor 1040-6 may include a light emission unit and a camera that functions to receive light, wherein the iris sensor outputs light through the light emission unit, acquires an image through the camera that receives reflected light, and transfers the acquired image to the processor 1010. In the iris sensor 1040-6, the light emission unit and the camera may be spaced apart from each other by a predetermined interval in order to recognize an accurate iris shape. For example, in the iris sensor 1040-6, an IR camera module may receive light emitted from the light emission unit to acquire an image of a predetermined pixel (e.g., 200 pixels) or higher, an image suitable for iris recognition may be selected through pre-processing of the acquired image, and the selected image may be transferred to the processor 1010. The processor 1010 may perform iris recognition by improving the image, that is transferred by the iris sensor 1040-6, to an image appropriate for iris recognition in order to extract an iris area, extracting a uniquely coded binary value from an extracted iris image, and then performing comparison with a previously stored iris image, thereby determining whether the comparison shows a match.

According to an embodiment, the biometric sensor 1040-8 may include a light emission unit and a light reception unit, may output light to a living body through the light emission unit, and may sense light reflected by the living body through the light reception unit so as to transfer a sensing result to the processor 1010. The processor 1010 may acquire biometric information by using the sensing result transferred by the biometric sensor 1040-8. For example, the biometric sensor 1040-8 may include a heart rate sensor (capable of measuring heart rate, stress, and oxygen saturation), a fingerprint sensor, a blood glucose sensor, a blood pressure sensor, and the like.

According to various embodiments, a method for controlling sensitivity of a sensor on the basis of a window attribute in the electronic device may include: on the basis of at least one attribute determined from among a plurality of attributes, identifying control information related to an operation of changing an attribute of at least a partial area of a window cover, in which the attribute of at least the partial area may be changed via an electrical control; determining a sensitivity related to at least one sensor at least on the basis of the control information; and acquiring peripheral information of the exterior of the electronic device by using the at least one sensor, at least one the basis of the determined sensitivity.

According to an embodiment, acquiring of the peripheral information may include: adjusting a setting value related to receiving external light by the at least one sensor, at least on the basis of the determined sensitivity; and on the basis of the adjusted setting value, acquiring information related to illuminance at least on the basis of sensing of the light received by the at least one sensor.

According to an embodiment, acquiring the peripheral information may include: adjusting a setting value related to proximity sensing performed by the at least one sensor, on the basis of the determined sensitivity; performing control to output light and to receive the light after being reflected by an external object, by the at least one sensor on the basis of the adjusted setting value; and determining a proximity of the external object at least on the basis of sensing of the reflected light.

According to an embodiment, acquiring the peripheral information may include: adjusting a setting value related to iris recognition performed by the at least one sensor, on the basis of the determined sensitivity; outputting light on the basis of the adjusted setting value and receiving the light after being reflected by an external object in order to acquire an image; and determining an iris from the acquired image at least one the basis of sensing of the reflected light. According to an embodiment, as at least a part of changing on the basis of the at least one attribute, at least one of a color, a texture, and a pattern of at least the partial area may be set to be changed.

According to an embodiment, at least a part of determining the sensitivity may include: identifying a light transmissivity of at least the partial area, which corresponds to the at least one attribute; and adjusting setting of the at least one sensor on the basis of at least one setting value corresponding to the identified light transmissivity from among one or more setting values according to the light transmissivity of at least the partial area.

According to an embodiment, as at least a part of acquiring the peripheral information of the exterior of the electronic device, it may be set to adjust a sensing value acquired using the at least one sensor, at least on the basis of the determined sensitivity.

Figure 11:
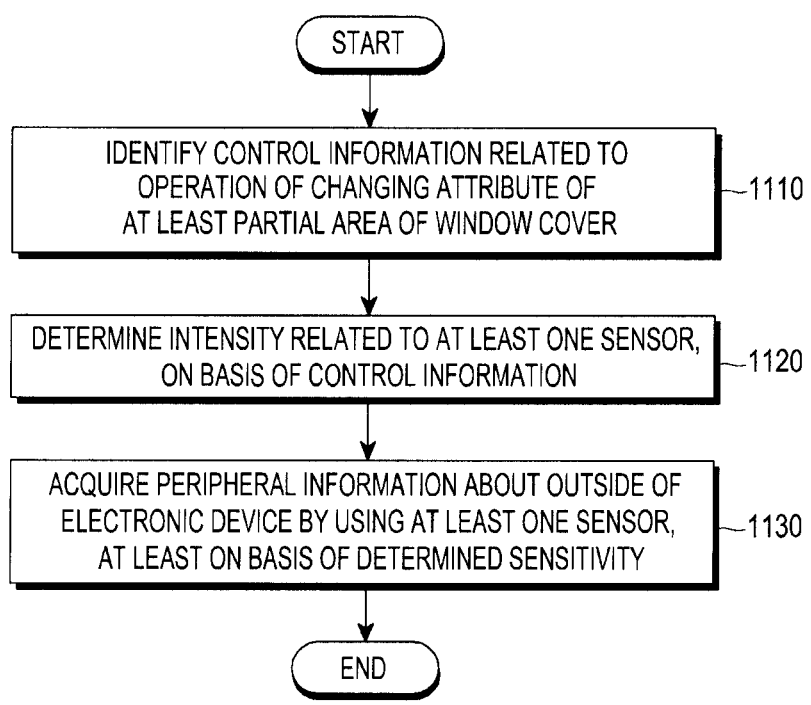
FIG. 11 is a flow chart for an operation of controlling at least one sensor disposed below a smart window in an electronic device according to various embodiments.

FIG. 11 is a flow chart for an operation of controlling at least one sensor disposed below a smart window in an electronic device according to various embodiments.

Referring to FIG. 11, an electronic device according to an embodiment may include all or some of the electronic device 101 in FIG. 1, the electronic device 201 in FIG. 2, the electronic device 401 in FIG. 4, and the electronic device 1001 in FIG. 10.

A processor of the electronic device (e.g., reference numeral 120 in FIG. 1, 210 in FIG. 2, or 1010 in FIG. 10) may identify, in operation 1110, control information related to an operation of changing an attribute of at least partial area of a window cover (e.g., reference numeral 402 in FIG. 4, 502*a* in FIG. 5A, 502*b* in FIG. 5B, 602 in FIG. 6, or 902 in FIG. 9).

According to various embodiments, the processor 1010 may transfer, to the smart window 1002, control information for controlling at least one attribute of at least a partial area of the window cover, e.g., the smart window 1002, on the basis of a user input, a function to be executed, an application type, or the like. According to an embodiment, the processor 1010 may include a smart window processor and may control the smart window 1002 through the smart window processor. According to an embodiment, the control information for controlling at least one attribute of the smart window 1002 may include control information for changing at least one of a color, a texture, and a pattern of the smart window 1002. In the smart window 1002, at least one attribute among the color, texture, and pattern thereof may be changed on the basis of the control information. According to an embodiment, the control information (hereinafter, also referred to as "first control information") for changing at least one of the color, texture, and pattern of the smart window 1002 may be stored in a memory (e.g., reference numeral 130 in FIG. 1, 230 in FIG. 2, or 1060 in FIG. 10). According to various embodiments, the processor may identify the first control information stored in the memory.

In operation 1120, the processor may determine a sensitivity related to at least one sensor at least on the basis of control information. According to an embodiment, the processor may determine a sensitivity related to at least one sensor disposed below the window cover on the basis of the first control information. According to an embodiment, the first control information may be color control information of the smart window 1002.

According to an embodiment, the processor may determine a setting value related to at least one sensor disposed below the smart window 1002 of the window cover on the basis of the first control information, for example, the color control information of the smart window 1002. According to an embodiment, the at least one sensor may be an optical-based sensor. The optical-based sensor may be one of an illuminance sensor, a proximity sensor, an iris sensor, and a biometric sensor.

According to an embodiment, a setting value for each of at least one sensor, which corresponds to color control information of the smart window 1002 may be stored as [TABLE 1] described below. The setting value in [TABLE 1] is an example, and various setting values may be stored according to various criteria.

TABLE 1

| | | Illuminance Sensor | | | | Proximity Sensor | |
| | | | | | | Recognition | Release |
| | | | | | | Threshold | Threshold |
| Color | ID | GF | Rcoef | Gcoef | Bcoef | Ccoef | Value | Value |
|---|---|---|---|---|---|---|---|---|
| Default | 0 | 222.4 | −9.2 | −59.9 | −8.5 | 66.6 | 31.3 | 20.6 |
| Black | 1 | 222.4 | −9.2 | −59.9 | −8.5 | 66.6 | 31.3 | 20.6 |
| Gold | 3 | 220.9 | −59.9 | −1.26 | 28.4 | 66.6 | 24 | 16 |
| Silver | 4 | 144.8 | −55.4 | −36.2 | −64.8 | 66.6 | 29.3 | 22 |
| Blue | 6 | 235.6 | −52.2 | −32.2 | −8.1 | 66.6 | 30 | 20 |
| PinkGold | 7 | 134.4 | −58.1 | 7.4 | −3.4 | 66.6 | 27.3 | 18.6 |

According to various embodiments, as illustrated in [TABLE 1], a color identifier (ID: identification) and a sensor setting value corresponding to the color identifier may be stored for each color of the smart window. According to an embodiment, a color of the smart window may be black, gold, silver, blue, silver-gold, or the like, an ID may be assigned to each color, and a setting value corresponding to each sensor may be stored for each color ID. For example, the color of the smart window is not limited to the above embodiment, and may be set to various colors.

According to an embodiment, a setting value corresponding to the illuminance sensor may include a gain factor (GF) value, an Rcoef value, a Gcoef value, a Bcoef value, and a Ccoef value. For example, the GF value, the Rcoef value, the Gcoef value, the Bcoef value, and the Ccoef value may be illuminance constant values. The GF value may be an illuminance constant value corresponding to a gain factor, the Rcoef value is an illuminance constant value corresponding to an R value, the Gcoef value is an illuminance constant value corresponding to a G value, the Bcoef value is an illuminance constant value corresponding to a V value, and the Ccoef value is an illuminance constant value corresponding to a C value. According to an embodiment, the processor may determine a sensitivity to the illuminance sensor by adjusting the GF value, the Rcoef value, the Gcoef value, the Bcoef value, and the Ccoef value according to color control information. The processor may calculate an illuminance (Lux) value by using the adjusted GF value, Rcoef value, Gcoef value, Bcoef value, and Ccoef values, which are obtained by adjusting as the GF value, the Rcoef value, the Gcoef value, the Bcoef value, and the Ccoef values according to the color control information. For example, the illuminance (Lux) value may be calculated according to [MATHEMATICAL EQUATION 1] described below.

$$lux = DGFx(R*Rcoef + G*Gcoef + B*Bcoef + C*Ccoef) \quad \text{[MATHEMATICAL EQUATION 1]}$$

According to an embodiment, a setting value corresponding to the proximity sensor may include a recognition threshold value and a release threshold value. For example, the recognition threshold value may be an analog-digital converter (ADC) value that determines proximity recognition of an external object by the proximity sensor. The release threshold value may be an ADC value that determines proximity release of an external object. According to an embodiment, the processor may determine a sensitivity of the proximity sensor by using the recognition threshold value and the release threshold value.

Although setting values corresponding to the illuminance sensor and the proximity sensor have been described in [TABLE 1], the respective setting values of the iris sensor and the biosensor may also be stored in the same manner as the setting values corresponding to the illuminance sensor and the proximity sensor.

For example, a setting value corresponding to the iris sensor may include a current, a light emission unit output time (pulse length), and a light reception time (integration time), and the processor may determine a sensitivity of the iris sensor by using at least some setting values of the current, the light emission unit output time, and the light reception time.

In operation 1130, the processor may acquire peripheral information of the exterior of the electronic device by using the at least one sensor, at least on the basis of the determined sensitivity.

According to an embodiment, the processor may acquire peripheral information of the exterior of the electronic device by using the at least one sensor, on the basis of the setting values according to the determined sensitivity. For example, the processor may acquire illuminance information by using the illuminance sensor, on the basis of the setting values according to the determined sensitivity. According to an embodiment, the processor may acquire proximity information by using the proximity sensor, on the basis of the setting values according to the determined sensitivity. According to an embodiment, and the processor may acquire iris information by using the iris sensor, on the basis of the setting values according to the determined sensitivity. According to an embodiment, the processor may acquire biometric information by using the biometric sensor, on the basis of the setting values according to the determined sensitivity.

According to various embodiments, the setting values according to the determined sensitivity may be determined according to a wavelength-specific transmissivity on the basis of the color of the smart window 1002.

According to an embodiment, the wavelength-specific transmissivity on the basis of the color of the smart window 1002 may be as [TABLE 2] described below.

TABLE 2

| Color | ID | Wavelength | |
| --- | --- | --- | --- |
| | | 550 nm | 940 nm |
| Black | 1 | 7 ± 2.1% | 37 ± 5% |
| Gold | 2 | 8 ± 2.4% | 31 ± 6% |
| Silver | 4 | 12 ± 3.6% | 35 ± 7% |
| Blue | 6 | 11 ± 3.3% | 37 ± 5% |
| PinkGold | 7 | 12 ± 3.6% | 34 ± 7% |

Referring to [TABLE 2], for example, when the color of the smart window 1002 is black, a transmissivity at a wavelength of 550 nm may be 7±2.1% and a transmissivity at a wavelength of 940 nm may be 37±5%. When the color of the smart window 1002 is gold, a transmissivity at a wavelength of 550 nm may be 8±2.4% and a light transmissivity at a wavelength of 940 nm may be 31±6%. When the color of the smart window 1002 is silver, a transmissivity at a wavelength of 550 nm may be 12±3.6% and a transmissivity at a wavelength of 940 nm may be 35±7%. When the color of the smart window 1002 is blue, a transmissivity at a wavelength of 550 nm may be 11±3.3% and a transmissivity at a wavelength of 940 nm may be 37±5%. When the color of the smart window 1002 is pinkgold, a transmissivity at a wavelength of 550 nm may be 12±3.6% and a transmissivity at a wavelength of 940 nm may be 34±7%.

According to various embodiments, a wavelength-specific transmissivity may be designated according to the color of the smart window 1002. According to various embodiments, a setting value corresponding to at least one sensor may be designated on the basis of the wavelength-specific transmissivity, that is designated according to the color of the smart window 1002.

According to various embodiments, the GF value, the Rcoef value, the Gcoef value, the Bcoef value, and the Ccoef value, which are setting values corresponding to the illuminance sensor, may be determined on the basis of the wavelength-specific transmissivity determined according to the color of the smart window 1002. For example, when the color of the window 1002 is changed, the wavelength-specific transmissivity of three colors R, G, and B may be changed to correspond to the changed color, and the GF value, the Rcoef value, the Gcoef value, the Bcoef value, and the Ccoef value, which are setting values corresponding to the illuminance sensor, may be determined on the basis of the wavelength-specific transmissivity designated according to the color of the smart window 1002 so as to enable the wavelength-specific transmissivity of three colors R, G, and B to be constant as the wavelength-specific transmissivity for each of three colors R, G, and B is changed.

According to various embodiments, a recognition threshold value and a release threshold value, which are setting values corresponding to the proximity sensor, may be determined on the basis of the wavelength-specific transmissivity designated according to the color of the smart window 1002. For example, when the color of the smart window 1002 changes, the wavelength-specific transmissivity may be changed according to the changed color, and the recognition threshold value and the release threshold value, which are setting values correspond to the proximity sensor, may be determined on the basis of the wavelength-specific transmissivity designated according to the color of the smart window 1002 so as to enable a recognition distance and a release distance to be constant although the changed wavelength-specific transmissivity is changed.

According to various embodiments, at least a part of setting values among a current, a light emission unit output time (pulse length), a light reception time (integration time) may be determined on the basis of the wavelength-specific transmissivity designated according to the color of the smart window 1002. For example, when the color of the smart window 1002 changes, the wavelength-specific transmissivity may be changed to correspond to the changed color, and the at least a part of the current, the light emission unit output time (pulse length), and the light reception time (integration time), which are setting values corresponding to the iris sensor, may be determined on the basis of the wavelength-specific transmissivity designated according to the color of the smart window 1002 to enable an iris recognition distance to be constant although the changed wavelength-specific transmissivity is changed.

According to various embodiments, in a case where a setting value of the illuminance sensor is fixed to a setting value designated regardless of the color of the smart window 1002, when the color of the smart window 1002 changes, an average error rate of a reference illuminance (REF (lux)) and an illuminance (calculated lux) sensed and calculated by the illuminance sensor may increase.

According to an embodiment, when a setting value of the illuminance sensor is fixed to a setting value corresponding to the case where the color of the smart window 1002 is black, a result of illuminance information acquisition according to change in the color of the smart window 1002 may be as described in [TABLE 3] to [TABLE 5].

TABLE 3

| | Black | | | | | | | |
| --- | --- | --- | --- | --- | --- | --- | --- | --- |
| REF(lux) | 25 | 50 | 245 | 510 | 2495 | 5045 | 25050 | Average Error Rate |
| R | 15 | 35 | 170 | 360 | 175 | 3730 | 8855 | |
| G | 30 | 60 | 285 | 595 | 2905 | 5855 | 13885 | |
| B | 75 | 50 | 250 | 525 | 2590 | 5455 | 13260 | |
| C | 65 | 140 | 645 | 1365 | 6705 | 13875 | 33440 | |
| Calculated Lux | 25 | 55 | 230 | 490 | 2415 | 4950 | 23795 | |
| Error Rate | −5.75% | 5.05% | −5.46% | −3.45% | −3.18% | −1.87% | −5.01% | −2.81% |

[TABLE 3] may represent an error rate when the color of the smart window 1002 is black and a setting value of the illuminance sensor is set to correspond to the case where the color of the smart window 1002 is black.

Referring to [TABLE 3], since the setting value of the illuminance sensor is also set to a setting value corresponding to black that is the color of the smart window 1002, the average error rate of the reference illuminance (REF (lux)) and the illuminance (calculated lux) sensed and calculated by the illuminance sensor is about −2.81%, and therefore the error rate of less than +−5% may not be large.

TABLE 4

| | | | | Gold | | | | |
|---|---|---|---|---|---|---|---|---|
| REF(lux) | 25 | 50 | 245 | 510 | 2520 | 5050 | 25050 | Average Error Rate |
| R | 30 | 65 | 300 | 625 | 3060 | 6265 | 14875 | |
| G | 25 | 55 | 245 | 510 | 2475 | 4955 | 11715 | |
| B | 10 | 20 | 90 | 185 | 900 | 1770 | 4245 | |
| C | 60 | 125 | 590 | 1225 | 6005 | 12060 | 28795 | |
| Calculated Lux | 25 | 55 | 265 | 555 | 2720 | 5475 | 26140 | |
| Error Rate | 6.98% | 11.60% | 8.81% | 8.66% | 7.98% | 8.38% | 4.36% | 8.11% |

[TABLE 4] may represent an error rate when the color of the smart window 1002 is gold and a setting value of the illuminance sensor is set to correspond to the case where the color of the smart window 1002 is black.

Referring to [TABLE 4], since the color of the smart window 1002 is gold while a setting value of the illuminance sensor is set to correspond to black, the average error rate of the reference illuminance (REF (lux)) and the illuminance (calculated lux) sensed and calculated by the illuminance sensor is about 8.11%, and therefore the error rate may increase.

TABLE 5

| | | | | Blue | | | | |
|---|---|---|---|---|---|---|---|---|
| REF(lux) | 25 | 50 | 250 | 505 | 2510 | 5025 | 25050 | Average Error Rate |
| R | 40 | 90 | 430 | 875 | 4355 | 8960 | 315 | |
| G | 30 | 70 | 330 | 670 | 3325 | 6695 | 235 | |
| B | 15 | 30 | 15 | 310 | 1540 | 3115 | 110 | |
| C | 85 | 180 | 845 | 1735 | 8590 | 17305 | 625 | |
| Calculated Lux | 40 | 80 | 375 | 765 | 3780 | 7600 | 35400 | |
| Error Rate | 51.61% | 60.85% | 49.00% | 51.45% | 50.68% | 51.20% | 41.32% | 50.87% |

[TABLE 5] may represent an error rate when the color of the smart window 1002 is blue while a setting value of the illuminance sensor is set to correspond to the case where the color of the smart window 1002 is black.

Referring to [TABLE 5], since the color of the smart window 1002 is blue while a setting value of the illuminance sensor is set to correspond to black, the average error rate of the reference illuminance (REF (lux)) and the illuminance (calculated lux) sensed and calculated by the illuminance sensor is about 50.87%, and therefore the error rate may increase.

According to various embodiments, when a setting value of the illuminance sensor is set to a value corresponding to a color changed according to the color of the smart window 1002, the average error rate of the reference illuminance (REF (lux)) and the illuminance (calculated lux) sensed and calculated by the illuminance sensor may be small.

According to an embodiment, when a setting value of the illuminance sensor is changed according to the color of the smart window 1002, a result of illuminance information acquisition may be as described in [TABLE 6] and [TABLE 7].

TABLE 6

| | | | | Gold | | | | |
|---|---|---|---|---|---|---|---|---|
| REF(lux) | 25 | 50 | 245 | 510 | 2520 | 5050 | 25050 | Average Error Rate |
| R | 30 | 65 | 300 | 625 | 3060 | 6265 | 14875 | |
| G | 25 | 55 | 245 | 510 | 2475 | 4955 | 11715 | |
| B | 10 | 20 | 90 | 185 | 900 | 1770 | 4245 | |
| C | 60 | 125 | 590 | 1225 | 6005 | 12060 | 28795 | |
| Calculated Lux | 25 | 55 | 255 | 5250 | 2565 | 5115 | 24350 | |
| Error Rate | 2.21% | 8.63% | 3.10% | 2.99% | 1.79% | 1.33% | -2.79% | 2.47% |

[TABLE 6] may represent an error rate when the color of the smart window 1002 is gold and a setting value of the illuminance sensor is set to correspond to the case where the color of the smart window 1002 is gold.

Referring to [TABLE 6], since the setting value of the illuminance sensor is set corresponding to gold that is the color of the smart window 1002, the average error rate of the reference illuminance (REF (lux)) and the illuminance (calculated lux) sensed and calculated by the illuminance sensor is about 2.47%, and therefore the error rate of less than +−5% may not be large.

TABLE 7

| | Blue | | | | | | | |
|---|---|---|---|---|---|---|---|---|
| REF(lux) | 25 | 50 | 250 | 505 | 2510 | 5025 | 25050 | Average Error Rate |
| R | 40 | 90 | 430 | 875 | 4355 | 8960 | 315 | |
| G | 30 | 70 | 330 | 670 | 3325 | 6695 | 235 | |
| B | 15 | 30 | 15 | 310 | 1540 | 3115 | 110 | |
| C | 85 | 180 | 845 | 1735 | 8590 | 17305 | 625 | |
| Calculated Lux | 25 | 55 | 245 | 505 | 2490 | 4945 | 23360 | |
| Error Rate | 4.09% | 5.80% | −2.27% | −0.02% | −0.80% | −1.63% | −6.74% | −0.23% |

[TABLE 7] may represent an error rate when the color of the smart window 1002 is blue and a setting value of the illuminance sensor is set to correspond to the case where the color of the smart window 1002 is blue.

Referring to [TABLE 7], since the setting value of the illuminance sensor is set corresponding to blue that is the color of the smart window 1002, the average error rate of the reference illuminance (REF (lux)) and the illuminance (calculated lux) sensed and calculated by the illuminance sensor is about −0.23%, and therefore the error rate of less than +−5% may not be large.

According to various embodiments, in a case where a setting value of the proximity sensor is fixed to a setting value designated regardless of the color of the smart window 1002, a proximity recognition distance and a proximity release distance of the proximity sensor may not be constant as the color of the smart window 1002 changes.

TABLE 8

| Transmissivity (%) | Recognition Distance (mm) | Release Distance (mm) |
|---|---|---|
| 41.2 | 90.1 | 109.6 |
| 40.9 | 93.3 | 112.2 |
| 41.2 | 89.2 | 108.4 |
| 43.6 | 94 | 114.1 |
| 43.4 | 91.8 | 110 |
| 43.1 | 92.3 | 114.4 |
| 29.3 | 66.3 | 81.3 |
| 29.6 | 64.3 | 78.3 |
| 29.6 | 66.8 | 84.1 |
| 34.0 | 76.1 | 91.1 |
| 34.1 | 78.3 | 95 |
| 34.1 | 76.5 | 94 |

[TABLE 8] shows examples of the proximity recognition distance and the proximity release distance when a setting value of the proximity sensor is fixed to a designated setting value. Referring to [TABLE 8], the transmissivities according to the examples may be IR transmissivities, and the recognition distance and the release distance may be the proximity recognition distance and the proximity release distance, respectively. When a setting value of the proximity sensor is fixed to a designated setting value regardless of the color of the smart window 1002, the proximity recognition distance may be different by about 28 mm from a maximum 102.3 mm to a minimum 74.3 mm according to a transmissivity of the smart window, and the proximity release distance may be different by about 36.1 mm from a maximum of 124.4 mm to a minimum of 88.3 mm. Therefore, the difference between the proximity recognition distance and the proximity release distance may be large. Accordingly, when the proximity recognition distance and the proximity release distance are not constant, a sensing performance of the proximity sensor may not be maintained constant.

According to various embodiments, when a setting value of the proximity sensor changes to a setting value corresponding to a changed color of the smart window 1002 on the basis of a color change in the smart window 1002, the proximity recognition distance and the proximity release distance may be maintained relatively constant.

TABLE 9

| Transmissivity (%) | Recognition Distance (mm) | Release Distance (mm) |
|---|---|---|
| 41.2 | 58.9 | 78.2 |
| 40.9 | 62 | 81 |
| 41.2 | 58 | 77 |
| 43.6 | 62.5 | 82.9 |
| 43.4 | 60.6 | 78.7 |
| 43.1 | 61.1 | 83.1 |
| 29.3 | 58.9 | 73.9 |
| 29.6 | 56.8 | 71 |
| 29.6 | 59.5 | 76.7 |
| 34.0 | 59.3 | 74.1 |
| 34.1 | 61.5 | 78.2 |
| 34.1 | 59.7 | 77.2 |

[TABLE 9] shows examples of the proximity recognition distance and the proximity release distance when a setting value of the proximity sensor changes according to a color change in the smart window 1002. Referring to [TABLE 9], when the setting value of the proximity sensor changes according to the color of the smart window 1002, the proximity recognition distance may be different by about 5.7 mm from a maximum of 72.5 mm to a minimum of 66.8 mm according to a transmissivity of the smart window, and the proximity release distance may be different by about 13.1 mm from a maximum of 93.1 mm to a minimum of 81 mm, so that the difference between the proximity recognition distance and the proximity release distance may be small. Accordingly, when the proximity recognition distance and the proximity release distance are relatively constant, a sensing performance of the proximity sensor may be maintained constant.

Figure 12:
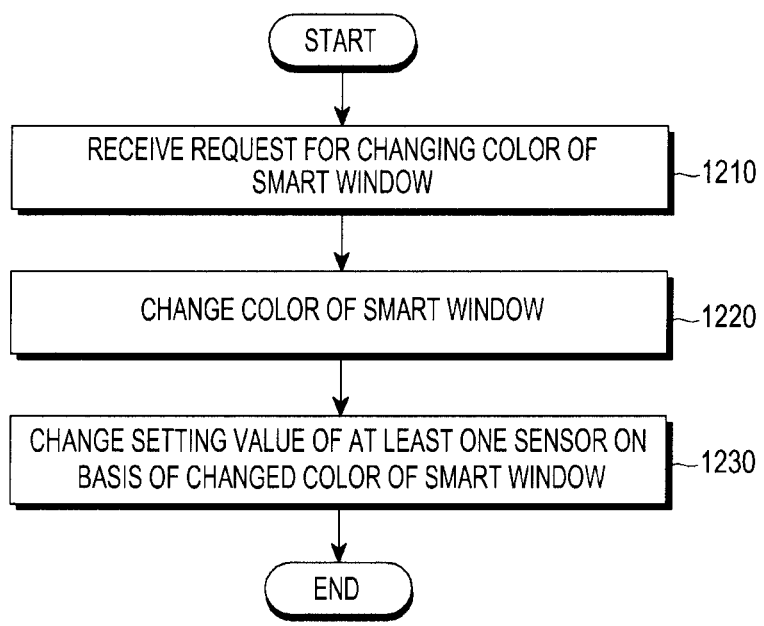
FIG. 12 is a flow chart for an operation of controlling a sensor on the basis of a color change in a smart window according to various embodiments.

FIG. 12 is a flow chart for an operation of controlling a sensor on the basis of a color change in a smart window according to various embodiments.

An electronic device according to an embodiment may include all or some of the electronic device 101 in FIG. 1, the electronic device 201 in FIG. 2, the electronic device 401 in FIG. 4, and the electronic device 1001 in FIG. 10.

A processor of the electronic device (e.g., reference numeral 120 in FIG. 1, 210 in FIG. 2, or 1010 in FIG. 10) may receive, in operation 1210, a request for a color change in a smart window. According to various embodiments, the processor may receive a request for the color change in the smart window, on the basis of a user input, a function to be executed, an application type, or the like.

The processor may change a color of the smart window in operation 1220. According to various embodiments, when a color change in the smart window is requested, the processor may transfer, to the smart window 1002, control information for controlling the color of the smart window to be changed. According to an embodiment, the control information for changing the color of the smart window 1002 may be stored in a memory (e.g., reference numeral 130 in FIG. 1, 230 in FIG. 2, or 1060 in FIG. 10). According to various embodiments, the processor may identify color control information stored in the memory to control the color of the smart window to be changed.

In operation 1230, the processor may change a setting value of at least one sensor on the basis of the changed color of the smart window. According to various embodiments, the processor may change a setting value relating to at least one sensor disposed below the smart window on the basis of the changed color of the smart window. According to various embodiments, the at least one sensor may be an optical-based sensor. The optical-based sensor may include at least one of an illuminance sensor, a proximity sensor, an iris sensor, and a biometric sensor.

According to various embodiments, setting values corresponding to the illuminance sensor, which are a GF value, an Rcoef value, a Gcoef value, a Bcoef value, and a Ccoef value, may be changed on the basis of a wavelength-specific transmissivity designated to a changed color in accordance with a color change in the smart window 1002. For example, when the color of the window 1002 changes, wavelength-specific transmissivities for three colors of R, G, and B may also be changed according to the changed color, and the setting values corresponding to the illuminance sensor, which are the GF value, the Rcoef value, the Gcoef value, the Bcoef value, and the Ccoef value, may be changed to enable the wavelength-specific transmissivities for three colors of R, G, and B to be constant as the wavelength-specific transmissivities for three colors of R, G, and B change.

According to various embodiments, as the color of the smart window 1002 changes, a recognition threshold value and a release threshold value, which are setting values corresponding to the proximity sensor, may be changed on the basis of a wavelength-specific transmissivity designated to the changed color. For example, when the color of the smart window 1002 changes, the wavelength-specific transmissivity may also be changed according to the changed color, and the recognition threshold value and the release threshold value, which are setting values corresponding to the proximity sensor, may be changed to enable a recognition distance and a release distance to be constant although the changed wavelength-specific transmissivity is changed.

According to various embodiments, as the color of the smart window 1002 changes, at least some setting values among a current, a light emission unit outputting time (pulse length), and a light reception time (integration time), which are setting values corresponding to the iris sensor, may be changed on the basis of a wavelength-specific transmissivity designated to the changed color. For example, when the color of the smart window 1002 changes, the wavelength-specific transmissivity may also be changed according to the changed color, and at least some setting values among the current, the light emission unit outputting time (pulse length), and light reception time (integration time), which are setting values corresponding to the iris sensor, may be changed to enable an iris recognition distance to be constant although the changed wavelength-specific transmissivity is changed.

According to various embodiments, although the color of the smart window 1002 changes, setting values corresponding to respective optical-based sensors, e.g., an illuminance sensor, a proximity sensor, an iris sensor, and a biometric sensor, may not be changed in a situation (e.g., a deactivated state) where each of the optical-based sensors is not used.

Figure 13:
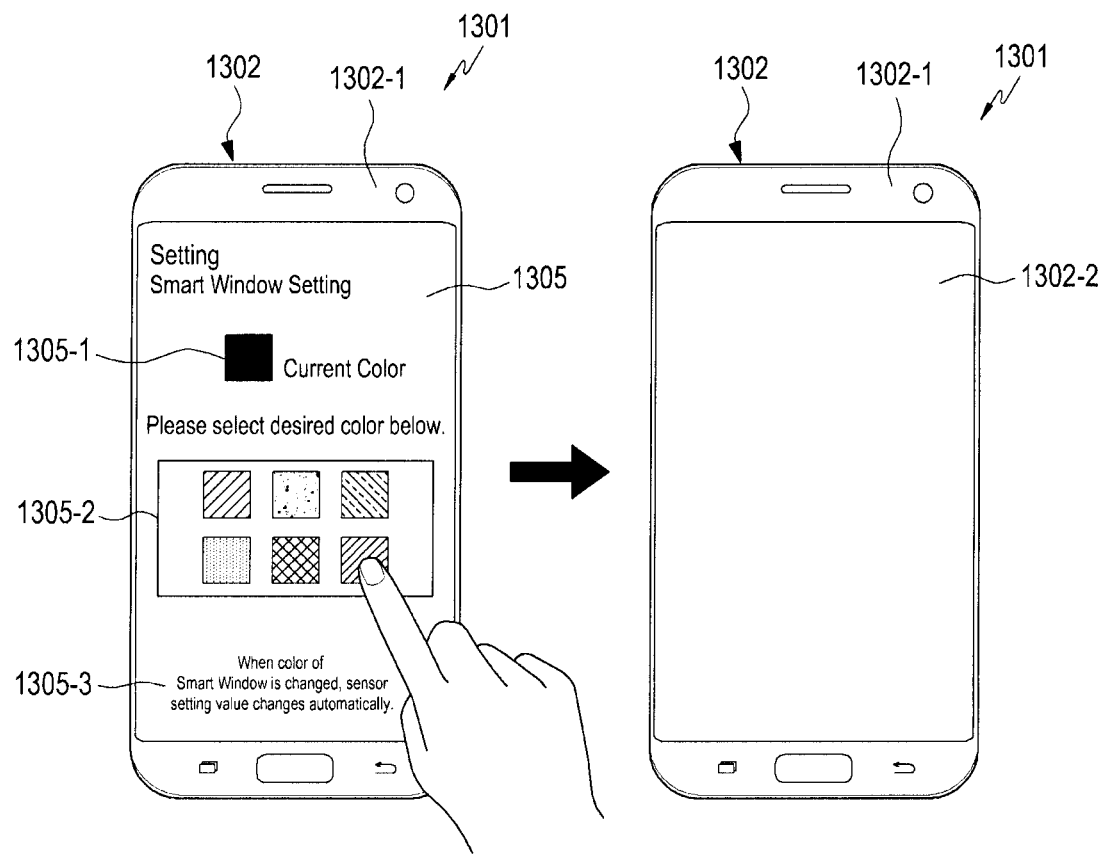
FIG. 13 is an example of a smart window color change screen according to various embodiments.

FIG. 13 is an example of a smart window color change screen according to various embodiments.

Referring to FIG. 13, an electronic device 1301 (e.g., reference numeral 101 in FIG. 1, 201 in FIG. 2, or 1001 in FIG. 10) according to an embodiment may display information 1305 related to a color change in a smart window 1302-1 on a screen area 1302-2.

According to various embodiments, the information related to a color change in the smart window 1302-1 may include at least one among current smart window color information 1305-1, changeable smart window color information 1305-2, and information 1305-3 notifying that a sensor setting value is changed, at the time of a color change in the smart window 1302-1. The information related to the smart window 1302-1 may include any information necessary for changing the color of the smart window 1302-1, in addition to the information above.

According to an embodiment, when a color is selected using the changeable smart window color information 1305-2, the electronic device 1301 may change the color of the smart window 1302-1 according to the selected color of the smart window. For example, when a gold color is selected in the changeable smart window color information 1305-2 by a user input, the electronic device 1301 may change the color of the smart window 1302-1 to the selected gold color.

According to an embodiment, the electronic device 1301 may change a setting value of at least one sensor disposed below the smart window 1302-1, simultaneously or sequentially with a color change in the smart window 1302-1. According to various embodiments, the at least one sensor may be an optical-based sensor. The optical-based sensor may include at least one of an illuminance sensor, a proximity sensor, an iris sensor, and a biometric sensor. For example, when the color of the smart window 1302-1 changes from a black color to a gold color, the electronic device 1301 may change a setting value of the at least one sensor disposed below the smart window 1302-1 from a setting value corresponding to the gold color to a setting value corresponding to the black color.

According to various embodiments, a method for controlling a sensor sensitivity on the basis of a display attribute in an electronic device may include: identifying control information relating to displaying of at least a partial area of a display; at least on the basis of the control information, determining a sensitivity related to at least one sensor disposed below at least the partial area of the display; and at least based in the determined sensitivity, acquiring peripheral information of the exterior of the electronic device by using the at least one sensor.

According to an embodiment, acquiring the peripheral information may include: at least on the basis of the determined sensitivity, adjusting a setting value related to receiving external light by the at least one sensor; on the basis of the adjusted setting value, acquiring information related to an illuminance at least on the basis of sensing of light received by the at least one sensor.

According to an embodiment, acquiring the peripheral information may include: on the basis of the determined sensitivity, adjusting a setting value related to proximity sensing performed by the at least one sensor; on the basis of the adjusted setting value, performing control to output light and receive the light after being reflected by an external object, by the at least one sensor; and determining a proximity of the external object at least on the basis of sensing the reflected light.

According to an embodiment, acquiring the peripheral information may include: on the basis of the determined sensitivity, adjusting a setting value related to iris recognition performed by the at least one sensor; on the basis of the adjusted setting value, outputting light and receiving the light after being reflected by an external object to acquire an image; and determining an iris from the acquired image, at least on the basis of sensing of the reflected light.

According to an embodiment, as at least a part of changing on the basis of the at least one attribute, at least one of a color, a texture, and a pattern of at least the partial area may be set to be changed.

According to an embodiment, at least a part of determining the sensitivity may include: identifying a light transmissivity of at least the partial area, which corresponds to the at least one attribute; and adjusting setting of the at least one sensor on the basis of at least one setting value corresponding to the identified light transmissivity from among one or more setting values according to the light transmissivity of at least the partial area.

According to an embodiment, as at least a part of acquiring the peripheral information of the exterior of the electronic device, it may be set to adjust a sensing value acquired using the at least one sensor, at least on the basis of the determined sensitivity.

Figure 14:
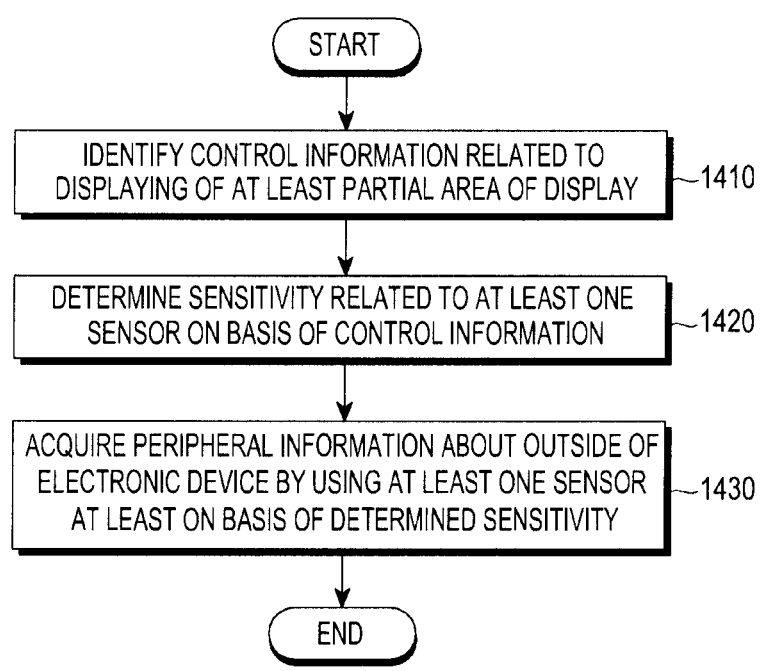
FIG. 14 is a flow chart for an operation of controlling at least one sensor disposed below a display in an electronic device according to various embodiments.

FIG. 14 is a flow chart for an operation of controlling at least one sensor disposed below a display in an electronic device according to various embodiments.

Referring to FIG. 14, an electronic device according to an embodiment may include all or some of the electronic device 101 in FIG. 1, the electronic device 201 in FIG. 2, the electronic device 401 in FIG. 4, and the electronic device 1001 in FIG. 10.

A processor of the electronic device (e.g., reference numeral 120 in FIG. 1, 210 in FIG. 2, or 1010 in FIG. 10) may identify, in operation 1410, control information related to displaying of at least the partial area of a display (e.g., reference numeral 160 in FIG. 1, 260 in FIG. 2, or 1020 in FIG. 10). For example, the processor may identify control information relating to a color or brightness which correspond to display information displayed in at least the partial area of the display. According to an embodiment, the control information related to displaying of at least the partial area of the display may include at least one of a color setting value for a color control in at least the partial area of the display and a brightness setting value for a brightness control in at least the partial area of the display. For example, the processor may identify the color setting value as the color of at least the partial area of the display is determined, or may identify the brightness setting value as the brightness of at least the partial area of the display is determined.

In operation 1420, the processor may determine a sensitivity related to the at least one sensor on the basis of the control information. According to an embodiment, the processor may determine the sensitivity related to the at least one sensor disposed below the display on the basis of the control information related to displaying of at least the partial area of a displaying area of the display. For example, the processor may determine the sensitivity of the at least one sensor on the basis of the identified color setting value or brightness setting value related to the color or brightness of the displaying area of the display by using information stored in a memory (e.g., reference numeral 130 in FIG. 1, 230 in FIG. 2, or 1060 in FIG. 10).

In operation 1430, at least on the basis of the determined sensitivity, the processor may acquire peripheral information of the exterior of the electronic device 1001 by using the at least one sensor disposed below at least the partial area of the display area of the display 1020. According to an embodiment, the processor may acquire the peripheral information of the exterior of the electronic device by using the at least one sensor, on the basis of the setting values according to the determined sensitivity. For example, the at least one sensor may include at least one of an illuminance sensor, a proximity sensor, an iris sensor, and a biometric sensor.

According to an embodiment, the processor may acquire illuminance information by using an illuminance sensor (e.g., reference numeral 1040-2 in FIG. 10), on the basis of setting values according to the determined sensitivity. According to an embodiment, the processor may acquire a proximity information by using a proximity sensor (e.g., reference numeral 1040-4 in FIG. 10), on the basis of setting values according to the determined sensitivity. According to an embodiment, the processor may acquire iris information by using an iris sensor (e.g., reference numeral 1040-6 in FIG. 10), on the basis of setting values according to the determined sensitivity. According to an embodiment, the processor may acquire biometric information by using a biometric sensor (e.g., reference numeral 1040-8 in FIG. 10), on the basis of setting values according to the determined sensitivity.

Each of the above-described component elements according to the present disclosure may be configured with one or more components, and the names of the corresponding component elements may vary on the basis of the type of electronic device. The electronic device according to various embodiments may include at least one of the aforementioned elements. Some elements may be omitted or other additional elements may be further included in the electronic device. Also, some of the components according to various embodiments may be combined into one entity, which may perform functions identical to those of the relevant components before the combination.

The term "module" as used herein may, for example, mean a unit including one of hardware, hardware programmed with software or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter.

According to various embodiments, at least some of the devices (e.g., modules or functions thereof) or the method (e.g., operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable storage medium may, for example, be the memory 130.

Various embodiments relate to a computer-readable recording medium having a program stored therein, the program configured to be executed by an electronic device including: a housing; a window cover housed in the housing, in which at least a partial area thereof may be changed via an electrical control on the basis of at least one attribute determined from among a plurality of attributes; at least one sensor disposed below at least the partial area; and a processor, wherein the processor is used to: identify control information corresponding to determination of an attribute of at least the partial area on the basis of the at least one attribute; determine a sensitivity related to the at least one sensor corresponding to the at least one attribute at least on the basis of the control information; and acquire peripheral information of the exterior of the electronic device by using the at least one sensor, at least on the basis of the determined sensitivity.

According to an embodiment, the electronic device may further include a memory that stores one or more setting values according to a light transmissivity of at least the partial area, and the program may use the processor to further perform, as at least a part of determining the sensitivity, identification of a light transmissivity of at least the partial area, which corresponds to the at least one attribute, and adjustment of setting of the at least one sensor on the basis of at least one setting value corresponding to the identified light transmissivity among the one or more setting values.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high class language codes, which can be executed in a computer by using an interpreter, as well as machine codes made by a compiler. The aforementioned hardware device may be configured to operate as one or more software modules in order to perform the operation, and vice versa.

The programming module according to the present disclosure may include one or more of the aforementioned components or may further include other additional components, or some of the aforementioned components may be omitted. Operations executed by a module, a programming module, or other component elements according to various embodiments may be executed sequentially, in parallel, repeatedly, or in a heuristic manner. Furthermore, some operations may be executed in a different order or may be omitted, or other operations may be added.

While the present disclosure has been shown and described with reference to certain embodiments thereof, it will be apparent to those skilled in the art that the camera lens module according to the present disclosure is not limited to these embodiments, and various changes in form and details may be made therein without departing from the spirit and scope of the present disclosure as defined by the appended claims.

What is claimed is:

1. An electronic device comprising:
    a housing;
    a window cover housed in the housing, wherein an attribute of at least a partial area of a window cover can be changed via an electrical control;
    at least one sensor disposed below the at least the partial area of the window cover; and
    at least one processor, wherein the at least one processor is configured to:
    identify control information related to changing the attribute of the at least the partial area of the window cover;
    identify a sensitivity from a plurality of sensitivities related to a sensing performance of the at least one sensor corresponding to the attribute of the at least the partial area based on the control information; and
    acquire peripheral information about the outside of the electronic device by using the at least one sensor, at least based on the identified sensitivity.

2. The electronic device of claim 1, wherein the at least one sensor comprises a light reception module, and the at least one processor is configured to adjust a setting value related to the light reception module based on the control information.

3. The electronic device of claim 1, wherein the at least one sensor comprises a light emission module for outputting light, and a light reception module for receiving the light after being reflected by an external object, wherein the at least one processor is configured to identify, as at least a part of acquiring of the peripheral information, a proximity of the external object based on sensing of the reflected light, by using the light reception module.

4. The electronic device of claim 3, wherein the processor is configured to identify at least one condition for identifying the proximity based on the control information.

5. The electronic device of claim 3, wherein the at least one processor is configured to identify at least one condition for identifying an iris based on the control information.

6. The electronic device of claim 1, wherein the at least one sensor comprises a light emission module for outputting light, and a camera module configured to receive the light after being reflected by an external object and acquire an image, wherein the at least one processor is configured to identify, as at least a part of acquiring of the peripheral information, an iris from the acquired image based on sensing of the reflected light, by using the camera module.

7. The electronic device of claim 1, wherein the at least one processor is configured to change, as at least a part of the changing based on the at least one attribute, at least one of a color, a texture, and a pattern of at least the partial area.

8. The electronic device of claim 1, further comprising:
    a memory configured to store one or more setting values according to a light transmissivity of at least the partial area,
    wherein the at least one processor is configured to:
    identify, as at least a part of identifying of the sensitivity, a light transmissivity of at least the partial area, which corresponds to the at least one attribute; and adjust setting of the at least one sensor based on at least one setting value corresponding to the light transmissivity among the one or more setting values in the memory.

9. The electronic device of claim 1, wherein the at least one processor is configured to adjust, as at least a part of acquiring of the peripheral information of an exterior of the electronic device, a sensing value acquired using the at least one sensor based on the identified sensitivity.

10. A non-transitory computer-readable recording medium, the non-transitory computer-readable recording medium having a program stored therein, the program configured to use the at least one processor to perform a method comprising:

identifying control information to change an attribute of a partial area of a window cover in an electronic device;

identifying a sensitivity from a plurality of sensitivities related to a sensing performance of at least one sensor of the electronic device corresponding to information on the attribute of the at least the partial area based on the control information; and acquiring peripheral information of an exterior of the electronic device by using the at least one sensor, at least based on the identified sensitivity.

11. The non-transitory computer-readable recording medium of claim 10, in the electronic device further comprising a memory configured to store one or more setting values according to a light transmissivity of at least the partial area, the non-transitory computer-readable recording medium having the program stored therein, the program configured to use the at least one processor to perform the method comprising:

identifying, as at least a part of identifying of the sensitivity, a light transmissivity of at least the partial area, which corresponds to the at least one attribute; and adjusting setting of the at least one sensor based on at least one setting value corresponding to the identified light transmissivity among the one or more setting values.

* * * * *